(12) United States Patent
Konetzki et al.

(10) Patent No.: US 8,044,046 B2
(45) Date of Patent: Oct. 25, 2011

(54) MEDICAMENTS FOR THE TREATMENT OF CHRONIC OBSTRUCTIVE PULMONARY DISEASE

(75) Inventors: Ingo Konetzki, Warthausen (DE); Kurt Schromm, Ingelheim am Rhein (DE); Hermann Schollenberger, Ingelheim am Rhein (DE); Sabine Pestel, Attenweiler (DE); Andreas Schnapp, Biberach (DE); Thierry Bouyssou, Warthausen (DE); Frank Buettner, Attenweiler (DE); Claudia Heine, Biberach (DE); Philipp Lustenberger, Basel (CH); Christoph Hoenke, Ingelheim (DE); Klaus Rudolf, Warthausen (DE)

(73) Assignee: Boehringer Ingelheim Pharma GmbH & Co KG, Ingelheim (DE)

( * ) Notice: Subject to any disclaimer, the term of this patent is extended or adjusted under 35 U.S.C. 154(b) by 0 days.

(21) Appl. No.: 11/132,075

(22) Filed: May 18, 2005

(65) Prior Publication Data
US 2005/0222144 A1    Oct. 6, 2005

Related U.S. Application Data

(63) Continuation of application No. 10/705,012, filed on Nov. 10, 2003, now Pat. No. 7,056,916.

(60) Provisional application No. 60/434,038, filed on Dec. 17, 2002.

(30) Foreign Application Priority Data

Nov. 15, 2002  (DE) ................... 102 53 282

(51) Int. Cl.
  C07D 265/36  (2006.01)
  A61K 31/538  (2006.01)
(52) U.S. Cl. .................... 514/230.5; 544/105
(58) Field of Classification Search ............ 514/230.5
  See application file for complete search history.

(56) References Cited

U.S. PATENT DOCUMENTS

| | | | |
|---|---|---|---|
| 4,215,119 A | 7/1980 | Mentrup et al. | |
| 4,252,951 A * | 2/1981 | Jackson et al. | 540/220 |
| 4,460,581 A * | 7/1984 | Schromm et al. | 514/211.08 |
| 4,570,630 A | 2/1986 | Elliott et al. | |
| 4,656,168 A | 4/1987 | Atkinson et al. | |
| 5,035,237 A | 7/1991 | Newell et al. | |
| 5,223,614 A | 6/1993 | Schromm et al. | |
| 5,472,143 A | 12/1995 | Bartels et al. | |
| 5,497,944 A | 3/1996 | Weston et al. | |
| 5,502,078 A | 3/1996 | Holloway et al. | |
| 5,750,701 A | 5/1998 | Beeley et al. | |
| 5,753,417 A | 5/1998 | Ulrich | |
| 5,911,851 A | 6/1999 | Bartels et al. | |
| 5,947,118 A | 9/1999 | Hochrainer et al. | |
| 5,955,058 A | 9/1999 | Jager et al. | |
| 5,964,416 A | 10/1999 | Jaeger et al. | |
| 5,998,430 A | 12/1999 | Schwantes et al. | |
| 6,007,676 A | 12/1999 | Bartels et al. | |
| 6,176,442 B1 | 1/2001 | Eicher et al. | |
| 6,453,795 B1 | 9/2002 | Eicher et al. | |
| 6,491,897 B1 | 12/2002 | Freund et al. | |
| 6,503,362 B1 | 1/2003 | Bartels et al. | |
| 6,582,678 B2 | 6/2003 | Staniforth | |
| 6,706,726 B2 | 3/2004 | Meissner et al. | |
| 6,747,154 B2 | 6/2004 | Brandenburg et al. | |
| 6,846,413 B1 | 1/2005 | Kadel et al. | |
| 6,905,239 B2 | 6/2005 | Boeck et al. | |
| 6,951,888 B2 | 10/2005 | Buettner et al. | |
| 7,056,916 B2 | 6/2006 | Konetzki et al. | |
| 7,084,153 B2 | 8/2006 | Banholzer et al. | |
| 7,135,500 B2 | 11/2006 | Konetzki et al. | |
| 7,160,882 B2 | 1/2007 | Bouyssou et al. | |
| 7,220,742 B2 | 5/2007 | Lustenberger et al. | |
| 7,244,728 B2 | 7/2007 | Bouyssou et al. | |

(Continued)

FOREIGN PATENT DOCUMENTS

CA    1180012 A    12/1984

(Continued)

OTHER PUBLICATIONS

R. S. Bedi Indian J. Chest Dis. Allied Sci. 2005; 47:243-244.*

(Continued)

Primary Examiner — Kahsay T Habte
(74) Attorney, Agent, or Firm — Michael P. Morris; Edouard G. Lebel; Wendy A. Petka

(57) ABSTRACT

A pharmaceutical composition comprising a compound of formula 1

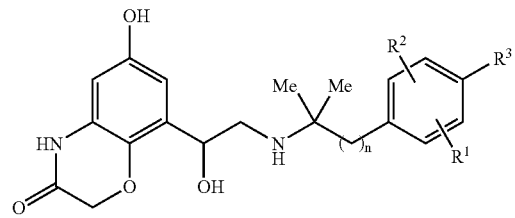

wherein:
n is 1 or 2;
$R^1$ is hydrogen, $C_1$-$C_4$-alkyl, halogen, OH, or —O—$C_1$-$C_4$-alkyl;
$R^2$ is hydrogen, $C_1$-$C_4$-alkyl, halogen, OH, or —O—$C_1$-$C_4$-alkyl;
$R^3$ is hydrogen, $C_1$-$C_4$-alkyl, OH, halogen, —O—$C_1$-$C_4$-alkyl, —O—$C_1$-$C_4$-alkylene-COOH, or —O—$C_1$-$C_4$-alkylene-CO—O—$C_1$-$C_4$-alkyl, or
an acid addition salt thereof with a pharmacologically acceptable acid, or a solvate or hydrate thereof; and
a pharmaceutically acceptable excipient or carrier, and methods for using the pharmaceutical formulation in the treatment of chronic obstructive pulmonary disease (COPD).

5 Claims, No Drawings

U.S. PATENT DOCUMENTS

| | | |
|---|---|---|
| 7,244,742 B2 | 7/2007 | Pieper et al. |
| 7,273,603 B2 | 9/2007 | Schmidt |
| 7,307,076 B2 | 12/2007 | Konetzki et al. |
| 7,332,175 B2 | 2/2008 | Konetzki |
| 7,375,104 B2 | 5/2008 | Bouyssou et al. |
| 7,417,051 B2 | 8/2008 | Banholzer et al. |
| 7,423,036 B2 | 9/2008 | Konetzki et al. |
| 7,429,583 B2 | 9/2008 | Bouyssou et al. |
| 7,491,719 B2 | 2/2009 | Lustenberger et al. |
| 7,727,984 B2 | 6/2010 | Konetzki et al. |
| 7,786,111 B2 | 8/2010 | Konetzki et al. |
| 2001/0008632 A1 | 7/2001 | Freund et al. |
| 2002/0002262 A1 | 1/2002 | Bier |
| 2002/0022625 A1 | 2/2002 | Walland et al. |
| 2002/0091115 A1 | 7/2002 | Dyatkin et al. |
| 2002/0115680 A1 | 8/2002 | Meissner et al. |
| 2002/0119991 A1 | 8/2002 | Meissner et al. |
| 2002/0189610 A1 | 12/2002 | Bozung et al. |
| 2003/0018019 A1 | 1/2003 | Meade et al. |
| 2003/0043687 A1 | 3/2003 | Boeck et al. |
| 2003/0119859 A1 | 6/2003 | Gavin |
| 2003/0152523 A1 | 8/2003 | Martin et al. |
| 2003/0207912 A1 | 11/2003 | Eickmeier et al. |
| 2004/0002502 A1 | 1/2004 | Banholzer et al. |
| 2004/0010003 A1 | 1/2004 | Banholzer et al. |
| 2004/0024007 A1 | 2/2004 | Pairet et al. |
| 2004/0044020 A1 | 3/2004 | Meade et al. |
| 2004/0048886 A1 | 3/2004 | Meade et al. |
| 2004/0048887 A1 | 3/2004 | Meade et al. |
| 2004/0058950 A1 | 3/2004 | Meade et al. |
| 2004/0087617 A1 | 5/2004 | Meissner et al. |
| 2004/0121996 A1 | 6/2004 | Barvian et al. |
| 2004/0122108 A1 | 6/2004 | Buettner et al. |
| 2004/0132759 A1 | 7/2004 | Konetzki et al. |
| 2004/0138307 A1 | 7/2004 | Konetzki et al. |
| 2004/0147513 A1 | 7/2004 | Konetzki et al. |
| 2004/0166065 A1 | 8/2004 | Schmidt |
| 2004/0228805 A1 | 11/2004 | Pieper et al. |
| 2005/0004228 A1 | 1/2005 | Konetzki |
| 2005/0008578 A1 | 1/2005 | Schmidt |
| 2005/0025718 A1 | 2/2005 | Meade et al. |
| 2005/0026948 A1 | 2/2005 | Meade et al. |
| 2005/0101625 A1 | 5/2005 | Boeck et al. |
| 2005/0137242 A1 | 6/2005 | Walland et al. |
| 2005/0154006 A1 | 7/2005 | Meade et al. |
| 2005/0165013 A1 | 7/2005 | Meade et al. |
| 2005/0186175 A1 | 8/2005 | Meade et al. |
| 2005/0239778 A1 | 10/2005 | Konetzki et al. |
| 2005/0255050 A1 | 11/2005 | Trunk et al. |
| 2005/0256114 A1 | 11/2005 | Grauert et al. |
| 2005/0256115 A1 | 11/2005 | Aven |
| 2005/0267106 A1 | 12/2005 | Lustenberger et al. |
| 2005/0272726 A1 | 12/2005 | Konetzki et al. |
| 2006/0003268 A1 | 1/2006 | Hong et al. |
| 2006/0057074 A1 | 3/2006 | Meade et al. |
| 2006/0063817 A1 | 3/2006 | Bouyssou et al. |
| 2006/0106213 A1 | 5/2006 | Konetzki et al. |
| 2006/0116398 A1 | 6/2006 | Mammen et al. |
| 2006/0189607 A1 | 8/2006 | Konetzki et al. |
| 2006/0222598 A1 | 10/2006 | Schmidt |
| 2007/0027148 A1 | 2/2007 | Lustenberger et al. |
| 2007/0066609 A1 | 3/2007 | Bouyssou et al. |
| 2007/0086957 A1 | 4/2007 | Bouyssou et al. |
| 2007/0088030 A1 | 4/2007 | Niklaus-Humke et al. |
| 2007/0088160 A1 | 4/2007 | Krueger et al. |
| 2007/0148598 A1 | 6/2007 | Colburn et al. |
| 2007/0155741 A1 | 7/2007 | Konetzki et al. |
| 2008/0041369 A1 | 2/2008 | Radau et al. |
| 2008/0041370 A1 | 2/2008 | Radau et al. |
| 2008/0063608 A1 | 3/2008 | Pieper et al. |
| 2008/0167298 A1 | 7/2008 | Konetzki et al. |
| 2008/0280897 A1 | 11/2008 | Aven |
| 2008/0293710 A1 | 11/2008 | Aven |
| 2009/0092558 A1 | 4/2009 | Konetzki et al. |
| 2009/0099225 A1 | 4/2009 | Freund et al. |
| 2009/0137578 A1 | 5/2009 | Lustenberger et al. |
| 2009/0155185 A1 | 6/2009 | Meade et al. |
| 2009/0181961 A1 | 7/2009 | Konetzki et al. |
| 2009/0185983 A1 | 7/2009 | Freund et al. |
| 2010/0009984 A1 | 1/2010 | Niklaus-Humke et al. |
| 2010/0022770 A1 | 1/2010 | Rodriguez Dehli et al. |
| 2010/0331288 A1 | 12/2010 | Aven et al. |

FOREIGN PATENT DOCUMENTS

| | | |
|---|---|---|
| CA | 2 164 222 C1 | 12/1994 |
| CA | 2225601 A1 | 1/1997 |
| CA | 2 232 151 A1 | 4/1997 |
| CA | 2233981 C1 | 4/1997 |
| CA | 2237853 C | 6/1997 |
| CA | 2275392 A1 | 12/1997 |
| CA | 2300908 A1 | 4/1999 |
| CA | 2 405 745 A1 | 11/2001 |
| CA | 2 450 961 A1 | 1/2003 |
| CA | 2 455 167 A1 | 1/2003 |
| CA | 2 425 539 A1 | 4/2003 |
| CA | 2 425 557 A1 | 4/2003 |
| CA | 2 471 578 A1 | 8/2003 |
| CA | 2 479 652 A1 | 9/2003 |
| CA | 2 481 876 A1 | 10/2003 |
| CA | 2492037 A1 | 1/2004 |
| CA | 2495454 A1 | 3/2004 |
| CA | 2501055 A1 | 4/2004 |
| CA | 2 506 082 A1 | 6/2004 |
| CA | 2506109 A1 | 6/2004 |
| CA | 2 558 067 A1 | 10/2005 |
| CA | 2 559 700 A1 | 11/2005 |
| CA | 2 564 379 A1 | 11/2005 |
| CA | 2559699 A1 | 11/2005 |
| CA | 2562859 A1 | 11/2005 |
| DE | 1 144 713 A1 | 3/1963 |
| DE | 1144713 | 3/1963 |
| DE | 36 25 685 A1 | 3/1987 |
| DE | 102004019540 A1 | 11/2005 |
| DE | 102004024454 A1 | 12/2005 |
| EP | 0072505 | 2/1983 |
| EP | 0 073 505 A1 | 3/1983 |
| EP | 0073505 A1 | 3/1983 |
| EP | 0 237 507 A1 | 9/1987 |
| EP | 0 321 864 A2 | 6/1989 |
| GB | 2106102 A | 4/1983 |
| JP | 09-012518 A | 1/1997 |
| JP | 11-255743 A | 9/1999 |
| WO | 9114468 A1 | 10/1991 |
| WO | 9407607 A1 | 4/1994 |
| WO | 9428958 A1 | 12/1994 |
| WO | 9701329 A1 | 1/1997 |
| WO | 9712683 A1 | 4/1997 |
| WO | 9712687 A1 | 4/1997 |
| WO | 9720590 A1 | 6/1997 |
| WO | 9827959 A2 | 7/1998 |
| WO | 9916530 A1 | 4/1999 |
| WO | 0158425 A2 | 8/2001 |
| WO | 0183462 A1 | 11/2001 |
| WO | 0230928 A1 | 4/2002 |
| WO | 0232899 A1 | 4/2002 |
| WO | 02/080884 A1 | 10/2002 |
| WO | 03000241 A2 | 1/2003 |
| WO | 03000265 A1 | 1/2003 |
| WO | 03/017970 A1 | 3/2003 |
| WO | 03064417 A1 | 8/2003 |
| WO | 03078429 A1 | 9/2003 |
| WO | 03084502 A1 | 10/2003 |
| WO | 2004000840 A2 | 12/2003 |
| WO | 2004004775 A1 | 1/2004 |
| WO | 2004/022058 A1 | 3/2004 |
| WO | 2004033412 A1 | 4/2004 |
| WO | 2004045618 A2 | 6/2004 |
| WO | 2004046083 | 6/2004 |
| WO | 2004087142 A1 | 10/2004 |
| WO | 2005014044 A1 | 2/2005 |
| WO | 2005/092870 A1 | 10/2005 |
| WO | 2005/102349 A1 | 11/2005 |
| WO | 2005/102350 A1 | 11/2005 |
| WO | 2005/110421 A2 | 11/2005 |
| WO | 2005/111005 A1 | 11/2005 |
| WO | 2007/020227 A1 | 2/2007 |
| WO | 2007/042153 A1 | 4/2007 |

| WO | 2007/148806 A1 | 12/2007 |
| WO | 2008/024045 A1 | 2/2008 |
| WO | 2009/059893 A1 | 5/2009 |

OTHER PUBLICATIONS http://www.postgradmed.com/issues/2005/03_05/martinez.htm, downloaded on Nov. 21, 2006.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
West, Anthony R., Solid State Chemistry and its Applications, Wiley, New York, 1988, pp. 358 & 365.*
Braga et al., "Making crystals from crystals: a green route to crystal engineering and polymorphism" ChemComm 2005, 3635-3645.*
Buettner, F. et al; "Betamimetics With A Prolonged Duration Of Activity, Processes For Preparing Them, And Their Use As Pharmaceutical Compositions"; U.S. Appl. No. 10/666,068, filed Sep. 19, 2003.
www.betterhealthcenter.com/allergy-asthma.htm: pp. 1 or 4 and 2 of 4; retrieved Mar. 26, 2006.
Gina: Global Initiative for Asthma: Pocket Guide for Asthma Management and Prevention (2005) pp. cov1-bc30.
Takayuki Hamada et al; Practical Synthesis of Optically Active Styrene Oxides Via reductive Transformation of 2-Chloroacetophenones with Chiral Rhodium Catalysts; Organic Letters (2002) vol. 4 No. 24 pp. 4373-4376.
Merck Manual Home Edition; Respiratory Distress Syndrome; Acidosis; Pneumococcal Infections; Lung Cancer and Severe Acute Respiratory Syndrome (SARS); retrieved Jun. 10, 2007.
Dutu, S. et al; Lung Function In COPD Patients Under Long Term Inhaled Therapy With Bronchodilator Agents and Beclometasone, European Respiratory Journal, (1997) Supp., Bd. 10, Nr. 25, Supp. 20.
Balzano, G. et al; "Effectiveness and Acceptability of a Domiciliary Multidrug Inhalation Treatment in Elderly Patients with Chronic Airflow Obstruction: Metered Dose Inhaler Versus Jet Nebulizer"; J. of Aerosol Medicine (2000) vol. 13, No. 1, 2000, pp. 25-33.
N. P. Buu-Hoi et al; Alpha, Alpha-Dimethyl-Beta-Arylethymanines, and Their Behavior in the Bischler-Napieralski Reaction; Journal of Organic Chemistry (1958) vol. 23, No. 1 pp. 42-45.
Masahide Yasuda et al; Redox-Photosensitized Aminations of 1,2-Benso-1,3-Cycloalkadienes, Arylcyclopropanes, and Quadricyclane with Ammonia; Journal of Organic Chemistry (2003) vol. 68, No. 20 pp. 7618-7624; American Chemistry Society.
D. Babin et al; A Biomimetic Synthesis of Chrysanthemol; (1981) vol. 37. No. 2 pp. 325-332.
Jack W. Timberlake et al; Thiadiaziridine 1,1-Dioxides: Synthesis and Chemistry; Journal of Organic Chemistry (1981) vol. 46, No. 10 pp. 2082-2089; American Chemical Society.
Ronald T. Coutts et al; Synthesis of Two in Vivo Metabolites of N-(N-Propyl)Phentermine; Canadian Journal of Chemistry (1978) vol. 56 pp. 3054-3058.
International Search Report PCT/EP2006/065217 mailed on Nov. 22, 2006.
Catherine M. Jackson et al; Benefit-Risk Assessment of Long-Acting B2-Agonists in Asthma; Drug Safety 2004 (2004) vol. 27 No. 4 pp. 243-270.
Milind P. Sovani et al; a Benefit-Risk Assessment of Inhaled Long-Acting B2-Agonists in the Management of Obstructive Pulmonary Disease; Drug Safety 2004 (2004) vol. 27 No. 10 pp. 689-715.
International Search Report PCT/EP2006/067122 mailed on Feb. 12, 2007.
International Search Report for PCT/EP2006/067126 mailed on Jun. 4, 2007.
W. L. F. Armarego; Purification of Laboratory Chemicals (4th Edition); (1997) p. 529; Elsevier Publisher.
International Search Report for equivalent international application PCT/EP03/12565 mailed on Aug. 4, 2004.
U.S. Appl. No. 11/275,730 filed Jan. 26, 2006.
U.S. Appl. No. 11/676,823 filed Feb. 20, 2007.
Final Office Action dated Mar. 8, 2007 from U.S. Appl. No. 11/109,030 filed Apr. 19, 2005.
International Search Report for PCT/EP2005/004075 mailed on Aug. 3, 2005.
International Search Report for PCT/EP2005/004073 mailed on Aug. 3, 2005.
International Search Report for PCT/EP2005/005079 mailed on Aug. 8, 2005.
U.S. Appl. No. 11/839,817 filed Aug. 16, 2007.
U.S. Appl. No. 11/839,809 filed Aug. 16, 2007.
International Search Report for PCT/EP2005/005028 mailed on Jan. 24, 2006.
Final Office Action dated Oct. 23, 2006 from U.S. Appl. No. 11/275,730 filed Jan. 26, 2006.
Non-Final Office Action dated Mar. 20, 2006 from U.S. Appl. No. 11/275,730 filed Jan. 26, 2006.
Non-Final Office Action dated Jun. 21, 2005 from U.S. Appl. No. 10/705,012 filed Nov. 10, 2003.
Non-Final Office Action dated Feb. 25, 2005 from U.S. Appl. No. 10/705,012 filed Nov. 10, 2003.
Non-Final Office Action dated Nov. 21, 2006 from U.S. Appl. No. 11/128,032 filed May 12, 2005.
Non-Final Office Action dated Dec. 28, 2005 from U.S. Appl. No. 11/128,032 filed May 12, 2005.
Declaration of Dr. Andreas Schnapp Under 37 C.F.R. § 1.132 submitted in U.S. Appl. No. 11/109,030 filed Apr. 19, 2005.
Non-Final Office Action dated Sep. 28, 2006 from U.S. Appl. No. 11/125,890 filed on May 10, 2005.
Final Office Action dated Mar. 1, 2007 from U.S. Appl. No. 11/125,890 filed May 10, 2005.
Non-Final Office Action dated Jul. 17, 2007 from U.S. Appl. No. 11/222,149 filed on Sep. 8, 2005.
Non-Final Office Action dated Nov. 29, 2007 from U.S. Appl. No. 11/109,030 filed on Apr. 19, 2005.
Non-Final Office Action dated Jan. 3, 2006 from U.S. Patent No. 7,160,882 B2.
Non-Final Office Action dated Jun. 5, 2006 from U.S. Patent No. 7,160,882 B2.
Non-Final Office Action dated Jun. 4, 2007 from U.S. Appl. No. 11/600,417 filed on Nov. 15, 2006.
Response to Office Action filed Dec. 12, 2007 from U.S. Appl. No. 11/128,141 filed May 12, 2005.
Non-Final Office Action dated Mar. 24, 2008 from U.S. Appl. No. 11/128,141 filed on May 12, 2005.
Sudha R. Vippagunta, et al; Crystalline Solids; Advanced Delivery Reviews (2001) vol. 48, pp. 3-26.
Non-Final Office Action dated Mar. 28, 2008 from U.S. Appl. No. 11/543,168 filed on Oct. 4, 2006.
Non-Final Office Action dated Apr. 3, 2008 from U.S. Appl. No. 11/543,694 filed on Oct. 5, 2006.
Non-Final Office Action dated Apr. 4, 2008 from U.S. Appl. No. 11/543,477 filed on Oct. 5, 2006.
Non-Final Office Action dated Sep. 22, 2008 from U.S. Appl. No. 11/109,030 filed Apr. 19, 2005.
Final Office Action dated Dec. 18, 2007 from U.S. Appl. No. 11/125,756 filed on May 10, 2005.
J. Bernstein; Controlling the Polymorphic Form Obtained; Polymorphism in Molecular Crystals in Chapter 3; Clarendon Press, Oxford, 2002, pp. 66-93.
J. Bernstein; Analytical Techniques for Studying and Characterizing Polymorphs; Analytical Techniques for Studying and Characterizing Polymorphs; Polymorphism in Molecular Crystals in Chapter 4; Clarendon Press, Oxford, 2002, pp. 94-150.
Harry G. Brittain, et al; Physical Characterization of Pharmaceutical Solids; Pharmaceutical Research (1991) vol. 8, pp. 963-973.
Harry G. Brittain, et al; Overview of Physical Characterization Methodology; Physical Characterization of Pharmaceutical Solids in Chapter 1; Marcel Dekker, New York, 1995, pp. 1-35.
Harry G. Brittain; Methods for the Characterization of Polymorphs and Solvates in Chapter 6; Polymorphism in Pharmaceutical Solids; Marcel Dekker, New York, 1999, pp. 227-278.

Harry G. Brittain; Solid State Analysis; Handbook of Modern Pharmaceutical Analysis in Chapter 3; Marcel Dekker, New York, 2001, pp. 57-84.

Harry G. Brittain; Preparation and identification of Polymorphs and Solvatomorphs; Preformulation in Solid Dosage Form Development; Informa Healthcare Press, New York, 2008, pp. 185-228.

David E. Bugay; Characterization of the Solid-State: Spectroscopic Techniques; Advanced Drug Delivery Reviews (2001) vol. 48, pp. 43-65.

Decision from the Board of Patent Appeals and Interferences in Appeal No. 2000-0600.

R. Hilfiker, et al; Polymorphism—Integrated Approach from High-Throughput Screening to Crystallization Optimization; Journal of Thermal Analysis and Calorimetry (2003) vol. 73, pp. 429-440.

Rolf Hilfiker, et al; Approaches to Polymorphism Screening; Polymorphism in the Pharmaceutical Industry in Chapter 11; Wiley-VCH, Mannheim, 2006, pp. 287-308.

International Patent Application PCT/EP2008/064201 filed under the PCT on Oct. 21, 2008.

Ulrich J. Griesser; The Importance of Solvates; Polymorphism: in the Pharmaceutical Industry (2006) vol. 8, pp. 211-233.

J. Keith Guillory; Generation of Polymorphs, Hydrates, Solvated, and Amorphous Solids; Marcel Dekker, New York, 1999, pp. 183-226.

Sherry L. Morissette, et al; High-Throughput Crystallization: Polymorphs, Salts, Co-Crystals and Solvates of Pharmaceutical Solids; Advanced Drug Delivery Reviews (2004) vol. 56, pp. 275-300.

Ann W. Newman, et al; Form Selection of Pharmaceutical Compounds; Handbook of Pharmaceutical Analysis in Chapter 1; Marcel Dekker; New York, 2001, pp. 1-57.

Richard A. Storey, Pd.D., et al; Integration of High Throughput Screening Methodologies and Manual Processes for Solid Form Selection; American Pharmaceutical Review (2003) pp. 100-105.

Terence L. Threlfall; Analysis of Organic Polymorphs: A Review; Analyst (1995) vol. 120, pp. 2435-2460.

Calvo, G. Mario; Is It Useful to Add an Anticholinergic Treatment to $\beta_2$-Adrenergic Medication in Acute Asthma Attack? Invest. Allergol Clin Immunol (1998) vol. 8, No. 1 pp. 30-34.

Declaration of Dr. Harry G. Brittain Under 37 C.F.R. § 1.132 submitted in U.S. Appl. No. 11/677,112 on Apr. 1, 2009 and in U.S. Appl. No. 11/132,075 on Apr. 3, 2009.

Derwent Publications Ltd. GB, Class B05, Nov. 10, 1998.

International Search Report PCT/EP2006/068191 mailed Feb. 5, 2007.

International Search Report PCT/EP2008/050800 mailed on Aug. 13, 2009.

Office Action dated Apr. 28, 2008 from U.S. Appl. No. 12/036,618 filed on Feb. 25, 2008.

Sereda, V.P., et al; Inhalation Therapy of Chronic Obstructive Lung Diseases; www.pharmindex.ru/practic/4_pulmo.html (2003) vol. 4, pp. 1-35.

U.S. Appl. No. 12/564,477 filed Sep. 22, 2009.

U.S. Appl. No. 12/522,008 filed Jul. 2, 2009.

Wolf, Manfred E; Burger's Medicinal Chemistry, 5ed, Part I, John Wiley & Sons, (1995) pp. 975-977.

Bertil Waldeck; Beta-Adrenoceptor Agonists and Asthma—100 Years of Development; European Journal of Pharmacology (2002) vol. 445 pp. 1-12.

Paul M. O'Byrne et al; Inhaled Beta 2-Agonists in the Treatment of Asthma; The New England Journal of Medicine (1996) vol. 335 No. 12 pp. 886-888.

International Search Report for PCT/EP2005/005078 mailed Oct. 28, 2005.

Office Action dated Apr. 18, 2007 from U.S. Appl. No. 11/125,756 filed May 10, 2005.

Office Action dated Jun. 14, 2007 from U.S. Appl. No. 11/128,141 filed May 12, 2005.

D. Ukena; Ciclesonide—A New Inhaled Corticosteroid. Pharmacological Properties and Clinical Efficacy in the Treatment of Asthma; Pneumalogie (2005) vol. 59 pp. 689-695.

Office Action dated May 24, 2007 from U.S. Appl. No. 11/677,112 filed Feb. 21, 2007.

Final Office Action dated Mar. 8, 2007 from U.S. Appl. No. 11/109,030 filed Apr. 19, 2005, already listed in the Information Disclosure Statement submitted on Aug. 20, 2007.

Klimans Klimanskaya, E.V.; Chronic Obstructive Lung Diseases in Children; http://www.nedug.ru/lib/lit/therap/01oct/therap204/therap.htm (2008) pp. 1-5.

Notice of Allowability dated Dec. 12, 2005 from U.S. Appl. No. 10/705,012 filed Nov. 10, 2003, now U.S. Patent No. 7,056,816.

Non-Final Office Action dated Apr. 30, 2008 from U.S. Appl. No. 11/677,112 filed Feb. 21, 2007.

Chronic Obstructive Pulmonary Disease (Wikipedia) Jul. 3, 2008.

U.S. Appl. No. 12/093,026 filed May 8, 2008.

U.S. Appl. No. 12/036,618 filed Feb. 25, 2008.

U.S. Appl. No. 12/133,066 filed Jun. 4, 2008.

Griesser, Ulrich J.; The Importance of Solvates; Polymorphism: in the Pharmaceutical Industry (2006) chapter 8; pp. 211-233.

Crapo, James D., et al. "Beta-Adrenergic Receptor Agonists", Baum's Textbook of Pulmonary Disease, 7th Edition, (2004) Lippincott Williams & Wilkins.

U.S. Appl. No. 13/021,946, filed Feb. 7, 2011, Inventor: Thomas Krueger.

U.S. Appl. No. 13/028,434, filed Feb. 16, 2011, Inventor: Thierry Bouyssou.

Final Office Action dated Jun. 28, 2011 in U.S. Appl. No. 11/109,094 filed on Apr. 19, 2005.

Final Office Action dated Mar. 11, 2011 from U.S. Appl. No. 12/407,982 filed Mar. 20, 2009.

Gold Pocket Guide, Jul. 2003.

Gold Pocket Guide, Jul. 2004.

Lovoilette, et al. "Montelukast Added to Inhaled Beclomethasone in Treatment of Asthma" Am J Respir Crit Care Med 1999, 160:1862-1868.

Nicholson, et al. "Involvement of steroid hormone and growth factor cross-talk in endocrine response in breast cancer" Endocrine-Related Cancer (1999) 6 373-387.

Non-Final Office Action dated Dec. 8, 2010 from U.S. Appl. No. 11/128,141 filed May 12, 2005.

Non-Final Office Action dated Mar. 16, 2011 from U.S. Appl. No. 12/133,066 filed Jun. 4, 2008.

Office Action dated Mar. 18, 2011, in U.S. Appl. No. 12/093,026 filed on Jul. 14, 2008.

Seddon, et al. "Pseudopolymorph: A Polemic" American Chemical Society (2004).

U.S. Appl. No. 13/087,009 filed Apr. 14, 2011. Inventor: Barbara Niklaus-Humke.

U.S. Appl. No. 13/155,062 filed Jun. 7, 2011. Inventor: Michael Trunk.

* cited by examiner

1

MEDICAMENTS FOR THE TREATMENT OF CHRONIC OBSTRUCTIVE PULMONARY DISEASE

RELATED APPLICATIONS

This application is a Continuation of U.S. application Ser. No. 10/705,012, filed Nov. 10, 2003 which now U.S. Pat. No. 7,056,916 claims priority to U.S. Ser. No. 60/434,038, filed Dec. 17, 2002, and German Application No. 102 53 282.6 filed Nov. 15, 2003, each of which is hereby incorporated by reference in its entirety.

FIELD OF THE INVENTION

The present invention relates to the use of the compounds of general formula 1

[Structure of formula 1 with OH, HN, O, Me, Me, N-H, OH, $R^1$, $R^2$, $R^3$ groups]

wherein the groups $R^1$, $R^2$, and $R^3$ may have the meanings given in the claims and in the specification, for preparing a pharmaceutical composition for the treatment of chronic obstructive pulmonary disease (COPD), as well as new compounds of general formula 1 and processes for preparing them.

BACKGROUND OF THE INVENTION

Betamimetics (β-adrenergic substances) are known from the prior art. Reference may be made, for example, to the disclosures of U.S. Pat. No. 4,460,581, which is hereby incorporated by reference, which proposes betamimetics for the treatment of a variety of complaints.

For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to taking the drug regularly at certain times of the day.

The aim of the present invention is therefore to provide betamimetics which have a therapeutic benefit in the treatment of COPD and are characterized by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day for treating COPD. In addition to the above objectives, the present invention also sets out to provide betamimetics which are not only exceptionally potent but are also characterized by a high degree of selectivity with respect to the $\beta_2$-adreno-receptor.

DETAILED DESCRIPTION OF THE INVENTION

Surprisingly it has been found that the abovementioned problems are solved by compounds of general formula 1.

Accordingly, the present invention relates to compounds of general formula 1

[Structure of formula 1 with OH, HN, O, Me, Me, N-H, OH, $R^1$, $R^2$, $R^3$ groups]

wherein:
n denotes 1 or 2,
$R^1$ denotes hydrogen, $C_1$-$C_4$-alkyl, halogen, OH, or —O—$C_1$-$C_4$-alkyl;
$R^2$ denotes hydrogen, $C_1$-$C_4$-alkyl, halogen, OH, or —O—$C_1$-$C_4$-alkyl; and
$R^3$ denotes hydrogen, $C_1$-$C_4$-alkyl, OH, halogen, —O—$C_1$-$C_4$-alkyl, —O—$C_1$-$C_4$-alkylene-COOH, or —O—$C_1$-$C_4$-alkylene-CO—O—$C_1$-$C_4$-alkyl,
for preparing a pharmaceutical composition for the treatment of COPD.

It is preferable to use compounds of general formula 1, wherein:
n denotes 1 or 2;
$R^1$ denotes hydrogen, halogen or $C_1$-$C_4$-alkyl;
$R^2$ denotes hydrogen, halogen or $C_1$-$C_4$-alkyl; and
$R^3$ denotes hydrogen, $C_1$-$C_4$-alkyl, OH, halogen, —O—$C_1$-$C_4$-alkyl, —O—$C_1$-$C_4$-alkylene-COOH, or —O—$C_1$-$C_4$-alkylene-CO—O—$C_1$-$C_4$-alkyl,
for preparing a pharmaceutical composition for the treatment of COPD.

It is preferable to use compounds of general formula 1 wherein:
n denotes 1 or 2;
$R^1$ denotes hydrogen, fluorine, chlorine or methyl;
$R^2$ denotes hydrogen, fluorine, chlorine or methyl; and
$R^3$ denotes hydrogen, $C_1$-$C_4$-alkyl, OH, fluorine, chlorine, bromine, —O—$C_1$-$C_4$-alkyl, —O—$C_1$-$C_4$-alkylene-COOH, or —O—$C_1$-$C_4$-alkylene-CO—O—$C_1$-$C_4$-alkyl,
for preparing a pharmaceutical composition for the treatment of COPD.

It is particularly preferred to use compounds of general formula 1 wherein:
n denotes 1 or 2;
$R^1$ denotes hydrogen, methyl or ethyl;
$R^2$ denotes hydrogen, methyl or ethyl; and
$R^3$ denotes hydrogen, methyl, ethyl, OH, methoxy, ethoxy, —O—$CH_2$—COOH, —O—$CH_2$—CO—O-methyl, or —O—$CH_2$—COOethyl,
for preparing a pharmaceutical composition for the treatment of COPD.

It is particularly preferred to use compounds of general formula 1 wherein:
n denotes 1 or 2;

R[1] denotes hydrogen or methyl;
R[2] denotes hydrogen or methyl; and
R[3] denotes hydrogen, methyl, OH, methoxy, —O—CH$_2$—COOH, or —O—CH$_2$—COOethyl, for preparing a pharmaceutical composition for the treatment of COPD.

Also of particular importance according to the invention is the use of compounds of general formula 1 wherein:
n denotes 1 or 2;
R[1] denotes hydrogen or methyl;
R[2] denotes hydrogen or methyl; and
R[3] denotes hydrogen, OH, methoxy, or —O—CH$_2$—COOH, for preparing a pharmaceutical composition for the treatment of COPD.

A preferred aspect of the present invention further relates to the use of compounds of general formula 1 wherein n is 1 and the groups R[1], R[2], and R[3] may have the abovementioned meanings, for preparing a pharmaceutical composition for the treatment of COPD.

Another preferred aspect of the present invention relates to the use of compounds of general formula 1 wherein n is 1 or 2, R[3] denotes a group selected from among hydrogen, OH, —O—C$_1$-C$_4$-alkyl, and —O—C$_1$-C$_4$-alkylene-COOH, and wherein the groups R[1] and R[2] may have the abovementioned meanings, for preparing a pharmaceutical composition for the treatment of COPD.

Another preferred aspect of the present invention relates to the use of compounds of general formula 1 wherein n is 2, R[1] and R[2] are each hydrogen, and the group R[3] may have the abovementioned meanings, for preparing a pharmaceutical composition for the treatment of COPD.

In the compounds of formula 1 the groups R[1] and R[2], if they do not represent hydrogen, may each be arranged in the ortho or meta position relative to the bond to the benzylic "—CH$_2$" group. If neither of the groups R[1] and R[2] denotes hydrogen, it is preferable according to the invention to use those compounds of formula 1 wherein the two groups R[1] and R[2] are either in the ortho configuration or both groups R[1] and R[2] are in the meta configuration, while the use of those compounds wherein both groups R[1] and R[2] are in the ortho configuration is particularly important.

In the compounds of formula 1 wherein one of the groups R[1] and R[2] does not denote hydrogen, it may be in the ortho or meta configuration with respect to the bond to the benzylic "—CH$_2$" group. In this case it is particularly preferred according to the invention to use those compounds of formula 1 wherein the group R[1] or R[2], which does not denote hydrogen, is in the ortho configuration.

In another aspect, the present invention relates to the abovementioned use of the compounds of formula 1 in the form of the individual optical isomers, mixtures of the individual enantiomers, or racemates. It is particularly preferable to use the compounds of formula 1 as mentioned above in the form of the enantiomerically pure compounds, while the use of the R enantiomers of the compounds of formula 1 is of particular importance according to the invention.

In another aspect, the present invention relates to the abovementioned use of the compounds of formula 1 in the form of the acid addition salts with pharmacologically acceptable acids as well as optionally in the form of the solvates and/or hydrates thereof.

The present invention further relates to the use of the abovementioned compounds of general formula 1 for preparing a pharmaceutical composition for once-a-day treatment of COPD.

Moreover, the present invention relates to a process for the treatment of COPD, characterized in that one or more of the abovementioned compounds of general formula 1 are administered in therapeutically effective amounts. The present invention also relates to processes for treating COPD, characterized in that one or more of the abovementioned compounds of general formula 1 are administered once a day in therapeutically effective amounts.

The compounds of general formula 1 are partly known from the prior art. Reference is made here to the disclosure of U.S. Pat. No. 4,460,581. In some cases, however, the compounds of general formula 1 have not yet been disclosed in the prior art. Another aspect of the present invention relates to these new compounds of formula 1 as such.

Accordingly, the present invention also relates to compounds of general formula 1

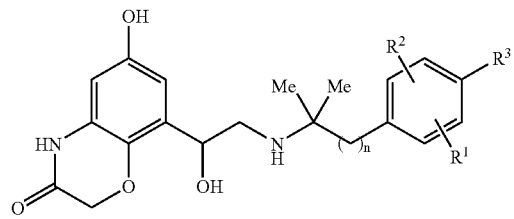

1 wherein:
n denotes 1;
R[1] denotes hydrogen, halogen, C$_1$-C$_4$-alkyl, or —O—C$_1$-C$_4$-alkyl;
R[2] denotes hydrogen, halogen, C$_1$-C$_4$-alkyl, or —O—C$_1$-C$_4$-alkyl; and
R[3] denotes C$_1$-C$_4$-alkyl, OH, halogen, —O—C$_1$-C$_4$-alkyl, —O—C$_1$-C$_4$-alkylene-COOH, or —O—C$_1$-C$_4$-alkylene-CO—O—C$_1$-C$_4$-alkyl,
with the proviso that, if R[1] and R[2] each represent ortho-methyl, R[3] cannot simultaneously be OH.

Preferred compounds of general formula 1 are those wherein:
n denotes 1;
R[1] denotes hydrogen, fluorine, chlorine, methyl, or methoxy;
R[2] denotes hydrogen, fluorine, chlorine, methyl, or methoxy; and
R[3] denotes C$_1$-C$_4$-alkyl, OH, fluorine, chlorine, bromine, —O—C$_1$-C$_4$-alkyl, —O—C$_1$-C$_4$-alkylene-COOH, or —O—C$_1$-C$_4$-alkylene-CO—O—C$_1$-C$_4$-alkyl,
with the proviso that, if R[1] and R[2] each represent ortho-methyl, R[3] cannot simultaneously be OH.

Preferred compounds of general formula 1 are those wherein:
n denotes 1;
R[1] denotes hydrogen or C$_1$-C$_4$-alkyl;
R[2] denotes hydrogen or C$_1$-C$_4$-alkyl; and
R[3] denotes C$_1$-C$_4$-alkyl, OH, —O—C$_1$-C$_4$-alkyl, —O—C$_1$-C$_4$-alkylene-COOH, or —O—C$_1$-C$_4$-alkylene-CO—O—C$_1$-C$_4$-alkyl,
with the proviso that, if R[1] and R[2] each represent ortho-methyl, R[3] cannot simultaneously be OH.

Preferred compounds of general formula 1 are those wherein:
n denotes 1;
R[1] denotes hydrogen, methyl or ethyl;
R[2] denotes hydrogen, methyl or ethyl; and
R[3] denotes methyl, ethyl, OH, methoxy, ethoxy, —O—CH$_2$—COOH, —O—CH$_2$—COOmethyl, or —O—CH$_2$—COOethyl, with the proviso that, if $R^1$ and $R^2$ each represent ortho-methyl, $R^3$ cannot simultaneously be OH.

Also preferred are the compounds of general formula 1 wherein:
n denotes 1;
$R^1$ denotes hydrogen or methyl;
$R^2$ denotes hydrogen or methyl; and
$R^3$ denotes methyl, OH, methoxy, —O—$CH_2$—COOH, or —O—$CH_2$—COOethyl,
with the proviso that if $R^1$ and $R^2$ each represent ortho-methyl, $R^3$ cannot simultaneously be OH.

Also preferred according to the invention are compounds of general formula 1 wherein $R^3$ denotes methoxy, ethoxy, —O—$CH_2$—COOH, —O—$CH_2$—COOmethyl, or —O—$CH_2$—COOethyl, and $R^1$, $R^2$, and n may have the above meanings.

The present invention also relates to compounds of general formula 1 wherein:
n denotes 1;
$R^1$ denotes halogen, $C_1$-$C_4$-alkyl, or —O—$C_1$-$C_4$-alkyl;
$R^2$ denotes halogen, $C_1$-$C_4$-alkyl, or —O—$C_1$-$C_4$-alkyl; and
$R^3$ denotes halogen, $C_1$-$C_4$-alkyl, or —O—$C_1$-$C_4$-alkyl.

The present invention also relates to compounds of general formula 1 wherein:
n denotes 1;
$R^1$ denotes fluorine, chlorine, methyl, or methoxy;
$R^2$ denotes fluorine, chlorine, methyl, or methoxy; and
$R^3$ denotes fluorine, chlorine, methyl, or methoxy.

In another preferred aspect the present invention relates to the compounds of general formula 1 wherein:
n denotes 1;
$R^1$ denotes hydrogen;
$R^2$ denotes hydrogen, fluorine, chlorine, or methyl; and
$R^3$ denotes methyl, ethyl, isopropyl, tert-butyl, OH, fluorine, chlorine, bromine, methoxy, ethoxy, —O—$CH_2$—COOH, —O—$CH_2$—$CH_2$—COOH, —O—$CH_2$—$CH_2$—$CH_2$—COOH, —O—$CH_2$—COOmethyl, —O—$CH_2$—COOethyl, —O—$CH_2$—$CH_2$—COOmethyl, —O—$CH_2$—$CH_2$—COOethyl, —O—$CH_2$—$CH_2$—$CH_2$—COOmethyl, or —O—$CH_2$—$CH_2$—$CH_2$—COOethyl.

Also particularly preferred are compounds of general formula 1 wherein
n denotes 1;
$R^1$ denotes hydrogen;
$R^2$ denotes hydrogen, fluorine, chlorine, or methyl; and
$R^3$ denotes OH, fluorine, chlorine, methyl, methoxy, ethoxy, or —O—$CH_2$—COOH.

Other particularly preferred compounds of general formula 1 according to the invention are those wherein
n denotes 1;
$R^1$ denotes hydrogen;
$R^2$ denotes halogen, $C_1$-$C_4$-alkyl, or —O—$C_1$-$C_4$-alkyl, preferably fluorine, chlorine, methoxy, or methyl; and
$R^3$ denotes halogen, $C_1$-$C_4$-alkyl, or —O—$C_1$-$C_4$-alkyl, preferably fluorine, chlorine, methoxy, or methyl.

Another preferred aspect of the present invention relates to the compounds of general formula 1 wherein n is 1, $R^1$ and $R^2$ denote hydrogen, and the group $R^3$ may have the abovementioned meanings.

Another preferred aspect of the present invention relates to the compounds of general formula 1 wherein:
n denotes 1;
$R^1$ and $R^2$ denote hydrogen; and
$R^3$ denotes methyl, ethyl, isopropyl, tert-butyl, OH, fluorine, chlorine, bromine, methoxy, ethoxy, —O—$CH_2$—COOH, —O—$CH_2$—$CH_2$—COOH, —O—$CH_2$—$CH_2$—$CH_2$—COOH, —O—$CH_2$—COOmethyl, —O—$CH_2$—COOethyl, —O—$CH_2$—$CH_2$—COOmethyl, —O—$CH_2$—$CH_2$—COOethyl, —O—$CH_2$—$CH_2$—$CH_2$—COOmethyl, or —O—$CH_2$—$CH_2$—$CH_2$—COOethyl.

Particularly preferred are compounds of general formula 1 wherein:
n denotes 1;
$R^1$ and $R^2$ denote hydrogen; and
$R^3$ denotes OH, fluorine, chlorine, methoxy, ethoxy, or —O—$CH_2$—COOH, preferably OH, fluorine, chlorine, ethoxy, or methoxy.

Particularly preferred are compounds of general formula 1 wherein:
n denotes 1;
$R^1$ and $R^2$ denote hydrogen; and
$R^3$ denotes fluorine, chlorine, methoxy, or ethoxy.

The present invention also relates to compounds of general formula 1 wherein:
n denotes 1;
$R^1$ denotes hydrogen, halogen, $C_1$-$C_4$-alkyl, or —O—$C_1$-$C_4$-alkyl;
$R^2$ denotes hydrogen, halogen, $C_1$-$C_4$-alkyl, or —O—$C_1$-$C_4$-alkyl; and
$R^3$ denotes hydrogen.

Also preferred are compounds of general formula 1 wherein:
n denotes 1;
$R^1$ denotes hydrogen, fluorine, chlorine, methyl, or methoxy;
$R^2$ denotes hydrogen, fluorine, chlorine, methyl, or methoxy; and
$R^3$ denotes hydrogen.

The present invention also relates to compounds of general formula 1 wherein:
n denotes 1;
$R^1$ denotes fluorine, chlorine, methyl, or methoxy;
$R^2$ denotes fluorine, chlorine, methyl, or methoxy; and
$R^3$ denotes hydrogen.

In the compounds of formula 1, the groups $R^1$ and $R^2$, if they do not represent hydrogen, may each be arranged in the ortho or meta position relative to the bond to the benzylic "—$CH_2$" group. If neither of the groups $R^1$ and $R^2$ denotes hydrogen, preferred compounds of formula 1 are those wherein the two groups $R^1$ and $R^2$ are either in the ortho configuration or both groups $R^1$ and $R^2$ are in the meta configuration, while the use of those compounds wherein both groups $R^1$ and $R^2$ are in the ortho configuration is particularly important.

In the compounds of formula 1 wherein one of the groups $R^1$ and $R^2$ does not denote hydrogen, it may be in the ortho or meta configuration with respect to the bond to the benzylic "—$CH_2$" group. In this case, particularly preferred compounds of formula 1 are those wherein the group $R^1$ or $R^2$, which does not denote hydrogen, is in the ortho configuration.

Also particularly preferred are compounds of general formula 1 which are selected from among:
(1) 6-hydroxy-8-{1-hydroxy-2-[2-(4-methoxyphenyl)-1,1-dimethylethylamino]ethyl}-4H-benzo[1,4]oxazin-3-one;
(2) 6-hydroxy-8-{1-hydroxy-2-[2-(4-phenoxyethylacetate)-1,1-dimethylethylamino]-ethyl}-4H-benzo[1,4]oxazin-3-one;
(3) 6-hydroxy-8-{1-hydroxy-2-[2-(4-phenoxyacetic acid)-1,1-dimethylethylamino]-ethyl}-4H-benzo[1,4]oxazin-3-one;
(4) 8-{2-[1,1-dimethyl-2-(2,4,6-trimethylphenyl)ethylamino]-1-hydroxyethyl}-6-hydroxy-4H-benzo[1,4]oxazin-3-one;
(5) 6-hydroxy-8-{1-hydroxy-2-[2-(4-hydroxyphenyl)-1,1-dimethylethylamino]ethyl}-4H-benzo[1,4]oxazin-3-one;

(6) 6-hydroxy-8-{1-hydroxy-2-[2-(4-isopropylphenyl)-1,1-dimethylethylamino]ethyl}-4H-benzo[1,4]oxazin-3-one;

(7) 8-{2-[2-(4-ethylphenyl)-1,1-dimethylethylamino]-1-hydroxyethyl}-6-hydroxy-4H-benzo[1,4]oxazin-3-one;

(8) 8-{2-[2-(4-fluoro-3-methylphenyl)-1,1-dimethylethylamino]-1-hydroxyethyl}-6-hydroxy-4H-benzo[1,4]oxazin-3-one;

(9) 8-{2-[2-(4-fluoro-2-methylphenyl)-1,1-dimethylethylamino]-1-hydroxyethyl}-6-hydroxy-4H-benzo[1,4]oxazin-3-one;

(10) 8-{2-[2-(2,4-difluorophenyl)-1,1-dimethylethylamino]-1-hydroxyethyl}-6-hydroxy-4H-benzo[1,4]oxazin-3-one;

(11) 8-{2-[2-(3,5-difluorophenyl)-1,1-dimethylethylamino]-1-hydroxyethyl}-6-hydroxy-4H-benzo[1,4]oxazin-3-one;

(12) 8-{2-[2-(4-ethoxyphenyl)-1,1-dimethylethylamino]-1-hydroxyethyl}-6-hydroxy-4H-benzo[1,4]oxazin-3-one;

(13) 8-{2-[2-(3,5-dimethylphenyl)-1,1-dimethylethylamino]-1-hydroxyethyl}-6-hydroxy-4H-benzo[1,4]oxazin-3-one;

(14) 4-(4-{2-[2-hydroxy-2-(6-hydroxy-3-oxo-3,4-dihydro-2H-benzo[1,4]oxazin-8-yl)-ethylmanino]-2-methylpropyl}phenoxy)butyric acid;

(15) 8-{2-[2-(3,4-difluorophenyl)-1,1-dimethylethylamino]-1-hydroxyethyl}-6-hydroxy-4H-benzo[1,4]oxazin-3-one;

(16) 8-{2-[2-(2-chloro-4-fluorophenyl)-1,1-dimethylethylamino]-1-hydroxyethyl}-6-hydroxy-4H-benzo[1,4]oxazin-3-one;

(17) 8-{2-[2-(4-chlorophenyl)-1,1-dimethylethylamino]-1-hydroxyethyl}-6-hydroxy-4H-benzo[1,4]oxazin-3-one;

(18) 8-{2-[2-(4-bromophenyl)-1,1-dimethylethylamino]-1-hydroxyethyl}-6-hydroxy-4H-benzo[1,4]oxazin-3-one;

(19) 8-{2-[2-(4-fluorophenyl)-1,1-dimethylethylamino]-1-hydroxyethyl}-6-hydroxy-4H-benzo[1,4]oxazin-3-one;

(20) 8-{2-[2-(4-fluoro-3-methoxyphenyl)-1,1-dimethylethylamino]-1-hydroxyethyl}-6-hydroxy-4H-benzo[1,4]oxazin-3-one;

(21) 8-{2-[2-(4-fluoro-2,6-dimethylphenyl)-1,1-dimethylethylamino]-1-hydroxyethyl}-6-hydroxy-4H-benzo[1,4]oxazin-3-one;

(22) 8-{2-[2-(4-chloro-2-methylphenyl)-1,1-dimethylethylamino]-1-hydroxyethyl}-6-hydroxy-4H-benzo[1,4]oxazin-3-one;

(23) 8-{2-[2-(4-chloro-3-fluorophenyl)-1,1-dimethylethylamino]-1-hydroxyethyl}-6-hydroxy-4H-benzo[1,4]oxazin-3-one;

(24) 8-{2-[2-(4-chloro-2-fluorophenyl)-1,1-dimethylethylamino]-1-hydroxyethyl}-6-hydroxy-4H-benzo[1,4]oxazin-3-one;

(25) 8-{2-[2-(3-chloro-4-fluorophenyl)-1,1-dimethylethylamino]-1-hydroxyethyl}-6-hydroxy-4H-benzo[1,4]oxazin-3-one;

(26) 8-{2-[2-(2,6-difluoro-4-methoxyphenyl)-1,1-dimethylethylamino]-1-hydroxyethyl}-6-hydroxy-4H-benzo[1,4]oxazin-3-one;

(27) 8-{2-[2-(2,5-difluoro-4-methoxyphenyl)-1,1-dimethylethylamino]-1-hydroxyethyl}-6-hydroxy-4H-benzo[1,4]oxazin-3-one;

(28) 8-{2-[2-(4-fluoro-3,5-dimethylphenyl)-1,1-dimethylethylamino]-1-hydroxyethyl}-6-hydroxy-4H-benzo[1,4]oxazin-3-one;

(29) 8-{2-[2-(3,5-dichlorophenyl)-1,1-dimethylethylamino]-1-hydroxyethyl}-6-hydroxy-4H-benzo[1,4]oxazin-3-one;

(30) 8-{2-[2-(4-chloro-3-methylphenyl)-1,1-dimethylethylamino]-1-hydroxyethyl}-6-hydroxy-4H-benzo[1,4]oxazin-3-one;

(31) 8-{2-[2-(3,4,5-trifluorophenyl)-1,1-dimethylethylamino]-1-hydroxyethyl}-6-hydroxy-4H-benzo[1,4]oxazin-3-one;

(32) 8-{2-[2-(3-methylphenyl)-1,1-dimethylethylamino]-1-hydroxyethyl}-6-hydroxy-4H-benzo[1,4]oxazin-3-one; and

(33) 8-{2-[2-(3,4-dichlorophenyl)-1,1-dimethylethylamino]-1-hydroxyethyl}-6-hydroxy-4H-benzo[1,4]oxazin-3-one.

In another aspect, the present invention relates to the abovementioned new compounds of formula 1 in the form of the individual optical isomers, mixtures of the individual enantiomers or racemates. Particularly preferred are compounds of formula 1 in the form of the enantiomerically pure compounds, while the R-enantiomers of the compounds of formula 1 are of exceptional importance according to the invention. Methods of separating racemates into the respective enantiomers are known in the prior art and may be used analogously to prepare the enantiomerically pure R- and S-enantiomers of the compounds of formula 1.

In another aspect, the present invention relates to the abovementioned compounds of formula 1 in the form of the acid addition salts with pharmacologically acceptable acids as well as optionally in the form of the solvates and/or hydrates thereof.

In another aspect, the present invention relates to the abovementioned compounds of formula 1 for use as pharmaceutical compositions. The present invention further relates to the use of the abovementioned new compounds of general formula 1 for preparing a pharmaceutical composition for the treatment of COPD. The present invention further relates to the use of the abovementioned new compounds of general formula 1 for preparing a pharmaceutical composition for the once-a-day treatment of COPD.

Moreover, the present invention relates to a process for the treatment of COPD, characterized in that one or more of the abovementioned compounds of general formula 1 are administered in therapeutically effective amounts. The present invention also relates to processes for treating COPD, characterized in that one or more of the abovementioned new compounds of general formula 1 are administered once a day in therapeutically effective amounts.

By acid addition salts with pharmacologically acceptable acids are meant, for example, the salts selected from among the hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydrooxalate, hydrosuccinate, hydrobenzoate, and hydro-p-toluenesulfonate salts, preferably the hydrochloride, hydrobromide, hydrosulfate, hydrophosphate, hydrofumarate, and hydromethanesulfonate salts. Of the abovementioned acid addition salts, the salts of hydrochloric acid, methanesulfonic acid, benzoic acid, and acetic acid are particularly preferred according to the invention.

For use according to the invention, the compounds of general formula 1 may optionally be used in the form of their individual optical isomers, mixtures of the individual enantiomers or racemates. If the compounds are used in enantiomerically pure form, the R-enantiomers are preferred.

Unless otherwise stated, the alkyl groups are straight-chained or branched alkyl groups having 1 to 4 carbon atoms. The following are mentioned by way of example: methyl, ethyl, propyl, or butyl. In some cases the abbreviations Me, Et, Prop, or Bu are used to denote the groups methyl, ethyl, propyl, or butyl. Unless otherwise stated, the definitions propyl and butyl include all the possible isomeric forms of the groups in question. Thus, for example, propyl includes n-propyl and isopropyl, butyl includes isobutyl, sec-butyl, and tert-butyl, etc.

Unless otherwise stated, the alkylene groups are branched and unbranched double-bonded alkyl bridges having 1 to 4 carbon atoms. The following are mentioned by way of example: methylene, ethylene, n-propylene, or n-butylene. Unless otherwise stated, the term alkyloxy groups (or —O-alkyl groups) denotes branched and unbranched alkyl groups having 1 to 4 carbon atoms which are linked via an oxygen atom. Examples of these include: methyloxy, ethyloxy, propyloxy, or butyloxy. The abbreviations MeO—, EtO—, PropO—, or BuO— are used in some cases to denote the groups methyloxy, ethyloxy, propyloxy, or butyloxy. Unless otherwise stated, the definitions propyloxy and butyloxy include all possible isomeric forms of the groups in question. Thus, for example, propyloxy includes n-propyloxy and iso-propyloxy, butyloxy includes isobutyloxy, sec-butyloxy, and tert-butyloxy, etc. In some cases, within the scope of the present invention, the term alkoxy is used instead of the term alkyloxy. Accordingly, the terms methoxy, ethoxy, propoxy, or butoxy may also be used to denote the groups methyloxy, ethyloxy, propyloxy, or butyloxy.

Halogen within the scope of the present invention denotes fluorine, chlorine, bromine, or iodine. Unless stated otherwise, fluorine, chlorine, and bromine are the preferred halogens.

The compounds according to the invention may be prepared analogously to methods already known from the prior art. Suitable methods of preparation are known for example from U.S. Pat. No. 4,460,581, to the entire contents of which reference is made at this point.

The examples of synthesis described below serve to illustrate compounds known from the prior art, which may surprisingly be used according to the present invention for the treatment of COPD.

EXAMPLE 1

6-hydroxy-8-{1-hydroxy-2-[2-(4-hydroxy-2,6-dimethylphenyl)-1,1-dimethylethylamino]ethyl}-4H-benzo[1,4]oxazin-3-one

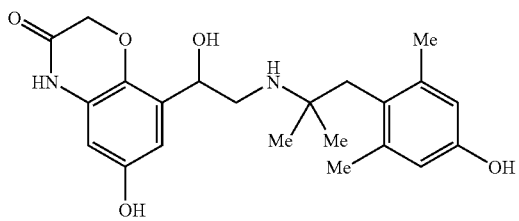

The compound is known from U.S. Pat. No. 4,460,581.

EXAMPLE 2

8-{2-[1,1-dimethyl-3-phenylpropylamnio]-1-hydroxyethyl}-6-hydroxy-4H-benzo[1,4]oxazin-3-one

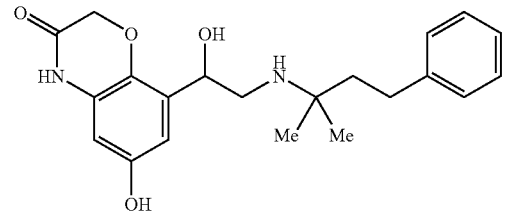

The compound is known from U.S. Pat. No. 4,460,581.

The examples of synthesis described below serve to illustrate new compounds according to the invention more fully. They are intended only as examples of procedure to illustrate the invention without restricting it to the subject matter described hereinafter.

EXAMPLE 3

6-hydroxy-8-{1-hydroxy-2-[2-(4-methoxyphenyl)-1,1-dimethylethylamino]-ethyl}-4H-benzo[1,4]oxazin-3-one

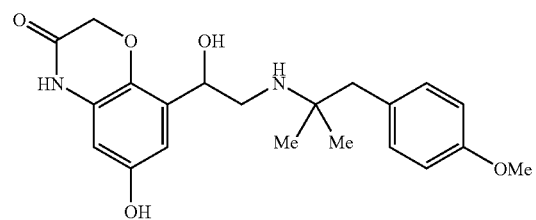

(a) 8-{2-[1,1-dimethyl-2-(4-methoxyphenyl)ethylamino]-1-hydroxyethyl}-6-benzyloxy-4H-benzo[1,4]oxazin-3-one 7.5 g of (6-benzyloxy-4H-benzo[1,4]oxazin-3-one)glyoxal hydrate is added at 70° C. to a solution of 3.6 g of 1,1-dimethyl-2-(4-methoxyphenyl)ethylamine in 100 mL ethanol and stirred for 15 minutes. Then 1 g of sodium borohydride is added within 30 minutes at 10° C. to 20° C. The mixture is stirred for one hour, combined with 10 mL acetone, and stirred for a further 30 minutes. The reaction mixture is diluted with 150 mL ethyl acetate, washed with water, dried with sodium sulfate, and evaporated down. The residue is dissolved in 50 mL methanol and 100 mL ethyl acetate and acidified with concentrated hydrochloric acid. After the addition of 100 mL diethyl ether, the product precipitates out. The crystals are filtered off, washed, and recrystallized in 50 mL ethanol. Yield: 7 g (68%; hydrochloride); melting point: 232° C.-234° C.

(b) 8-{2-[1,1-dimethyl-2-(4-methoxyphenyl)ethylamino]-1-hydroxyethyl}-6-hydroxy-4H-benzo[1,4]oxazin-3-one 6.8 g of the benzyl compound obtained above are hydrogenated in 125 mL methanol with the addition of 1 g palladium on charcoal (5%) at ambient temperature and under normal pressure. The catalyst is filtered off and the filtrate is freed from solvent. After recrystallization of the residue in 50 mL acetone and some water, a solid is obtained, which is filtered off and washed. Yield: 5.0 g (89%; hydrochloride); melting point: 155° C.-160° C.

The (R)- and (S)-enantiomers of Example 3 may be obtained from the racemate, for example, by chiral HPLC (e.g., column: Chirobiotic T, 250×22.1 mm made by Messrs Astec). The mobile phase may be methanol with 0.05% triethylamine and 0.05% acetic acid. Silica gel with a particle size of 5 μm, to which the glycoprotein Teicoplanin is covalently bound, can be used as the column material. Retention time (R-enantiomer): 40.1 minutes; retention time (S-enantiomer): 45.9 minutes. Both enantiomers are obtained according to this method in the form of their free base. The R-enantiomer of Example 3 is of exceptional importance according to the invention.

EXAMPLE 4

6-hydroxy-8-{1-hydroxy-2-[2-(4-phenoxyethyl acetate)-1,1-dimethylethylamino]ethyl}-4H-benzo[1,4]oxazin-3-one

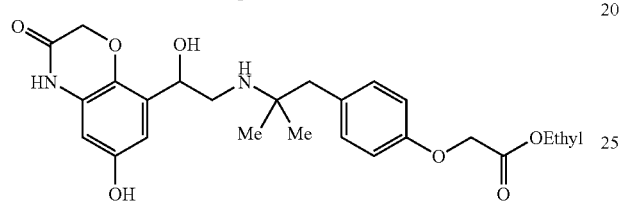

(a) 8-{2-[1,1-dimethyl-2-(4-phenoxyethyl acetate)ethylamino]-1-hydroxyethyl}-6-benzyloxy-4H-benzo[1,4]oxazin-3-one The title compound is obtained analogously to the method described in Example 3(a) from 15 g of (6-benzyloxy-4H-benzo[1,4]oxazin-3-one)glyoxal hydrate and 11.8 g of 1,1-dimethyl-2-(4-phenoxyethyl acetate)ethylamine hydrochloride. Yield: 16.5 g (69%, hydrochloride); melting point: 212° C.-214° C.

(b) 8-{2-[1,1-dimethyl-2-(4-phenoxyethyl acetate)ethylamino]-1-hydroxyethyl}-6-hydroxy-4H-benzo[1,4]oxazin-3-one 8 g of the benzyl alcohol obtained above is dissolved in 100 mL ethanol, 100 mL methanol, and 10 mL water and hydrogenated in the presence of 1 g palladium on charcoal (5%). After the theoretically calculated amount of hydrogen has been taken up, the catalyst is filtered off and the filtrate is evaporated down. The product which crystallizes out when the solvent is distilled off is suction filtered and washed. Yield: 5.5 g (81%; hydrochloride); melting point: 137° C.-140° C.

The (R)- and (S)-enantiomers of this example can be obtained by separating the racemate analogously to current methods of racemate cleaving known in the prior art.

EXAMPLE 5

6-hydroxy-8-{1-hydroxy-2-[2-(4-phenoxyacetic acid)-1,1-dimethylethylamino]ethyl}-4H-benzo[1,4]oxazin-3-one

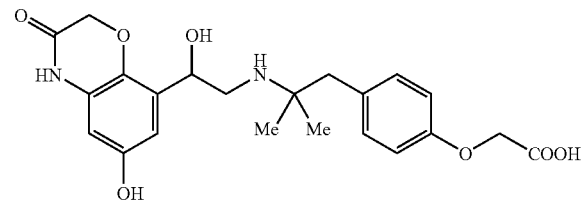

11 g of 8-{2-[1,1-dimethyl-2-(4-phenoxyethylacetate)ethylamino]-1-hydroxyethyl}-6-benzyloxy-4H-benzo[1,4]oxazin-3-one hydrochloride (Example 4(a)) is dissolved in 125 mL methanol and hydrogenated in the presence of 1 g palladium on charcoal (5%). After the theoretically calculated amount of hydrogen has been taken up, the catalyst is filtered off. 2.6 g of sodium hydroxide dissolved in 20 mL water is added to the filtrate. The mixture is refluxed for 30 minutes, the methanol is distilled off and combined with 10 mL water, 20 mL n-butanol, and 3.9 mL acetic acid. The solid precipitated is suction filtered and washed with diethyl ether. Yield: 7 g (87%). The hydrochloride is obtained by recrystallization from 0.5 molar hydrochloric acid. Melting point: 152° C.

The (R)- and (S)-enantiomers of this example can be obtained by separating the racemate analogously to current methods of racemate cleaving known in the prior art.

EXAMPLE 6

8-{2-[1,1-dimethyl-2-(2,4,6-trimethylphenyl)ethylamino]-1-hydroxyethyl}-6-hydroxy-4H-benzo[1,4]oxazin-3-one

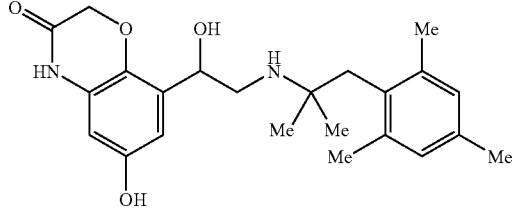

(a) 1-(6-benzyloxy-4H-benzo[1,4]oxazin-3-one)-2-[1,1-dimethyl-2-(2,4,6-trimethylphenyl)ethylimino]ethanone 7.2 g of (6-benzyloxy-4H-benzo[1,4]oxazin-3-one)glyoxal hydrate and 3.6 g of 1,1-dimethyl-2-(2,4,6-trimethylphenyl)ethylamine are heated to 70° C. for one hour in 100 mL ethanol. After cooling, the crystals precipitated are filtered off and washed with ethanol and diethyl ether. Yield: 8.6 g (94%); melting point: 175° C.

(b) 8-{2-[1,1-dimethyl-2-(2,4,6-trimethylphenyl)ethylamino]-1-hydroxyethyl}-6-benzyloxy-4H-benzo[1,4]oxazin-3-one 8.6 g of the Schiff base obtained according to Example 6(a) is dissolved in 100 mL ethanol and 20 mL THF, combined with 0.7 g sodium borohydride within 30 minutes at 10° C.-20° C., and stirred for one hour. After the addition of 10 mL acetone, the mixture is stirred for 30 minutes and then diluted with ethyl acetate and water. The product which crystallizes out on acidification with concentrated hydrochloric acid is filtered off and washed. Yield: 7.4 g (80%, hydrochloride); melting point: 235° C. (decomposition).

c) 8-{2-[1,1-dimethyl-2-(2,4,6-trimethylphenyl)ethylamino]-1-hydroxyethyl}-6-hydroxy-4H-benzo[1,4]oxazin-3-one 7.4 g of the benzyl compound obtained according to Example 6(b) is hydrogenated in 125 mL methanol with the addition of 1 g palladium on charcoal (5%) at ambient temperature under normal pressure. Then the catalyst is filtered off and the filtrate is evaporated down. The product which crystallizes out when acetone is added is suction filtered and washed with acetone and diethyl ether. Yield: 5 g (78%, hydrochloride); melting point 160° C. (decomposition).

The (R)- and (S)-enantiomers of this example can be obtained by separating the racemate analogously to current methods of racemate cleaving known in the prior art.

EXAMPLE 7

6-hydroxy-8-{1-hydroxy-2-[2-(4-hydroxyphenyl)-1,1-dimethylethylamino]-ethyl}-4H-benzo[1,4]oxazin-3-one

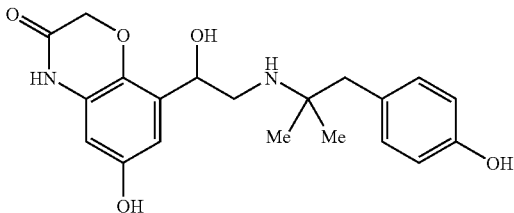

(a) 8-{2-[1,1-dimethyl-2-(4-hydroxyphenyl)ethylamino]-1-hydroxyethyl}-6-benzyloxy-4H-benzo[1,4]oxazin-3-one The title compound is prepared from 10 g of (6-benzyloxy-4H-benzo[1,4]oxazin-3-one)-glyoxal hydrate and 4.6 g of 1,1-dimethyl-2-(4-hydroxyphenyl)ethylamine analogously to the method for Example 3(a). Yield: 9.0 g (64%, hydrochloride); melting point: 255° C.-258° C.

(b) 8-{2-[1,1-dimethyl-2-(4-hydroxyphenyl)ethylamino]-1-hydroxyethyl}-6-hydroxy-4H-benzo[1,4]oxazin-3-one 5.7 g of the coupling product obtained above are hydrogenated in the presence of 0.6 g palladium on charcoal (5%) in 100 mL methanol. After the theoretically calculated amount of hydrogen has been taken up, the catalyst is filtered off and the filtrate is freed from solvent. The residue is dissolved in ethanol with heating and then combined with diethyl ether. The product precipitated is suction filtered and recrystallized once in water. Yield: 3.6 g (72%, hydrochloride); melting point: 159° C.-162° C.

The (R)- and (S)-enantiomers of this example can be obtained by separating the racemate analogously to current methods of racemate cleaving known in the prior art.

EXAMPLE 8

6-hydroxy-8-{1-hydroxy-2-[2-(4-isopropylphenyl)-1,1-dimethylethylamino]-ethyl}-4H-benzo[1,4]oxazin-3-one

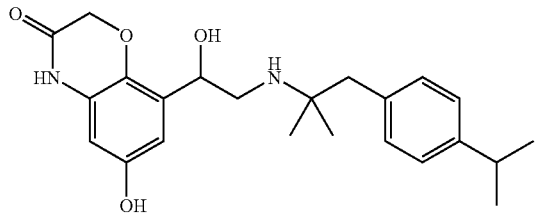

(a) 1-(4-isopropylphenyl)-2-methylpropan-2-ol

The reaction of a Grignard compound, prepared from 20 g (119 mmol) 4-isopropylbenzyl chloride, with 11.4 mL (155 mmol) acetone yields the target compound as a colorless oil. Yield: 13.0 g (57%); mass spectrometry: [M+H]$^+$=193.

(b) N-[2-(4-isopropylphenyl)-1,1-dimethylethyl]acetamide

A Ritter reaction is carried out with 10.2 g (53 mmol) of 1-(4-isopropylphenyl)-2-methylpropan-2-ol in the manner described for Example 9(b). The reaction mixture is poured onto ice water and made alkaline with sodium hydroxide solution, whereupon a solid is precipitated. This is suction filtered and dried. Yield: 9.90 g (80%); mass spectrometry: [M+H]$^+$=234.

(c) 2-(4-isopropylphenyl)-1,1-dimethylethyl amine

Reaction of 9.80 g (42 mmol) of N-[2-(4-isopropylphenyl)-1,1-dimethylethyl]acetamide analogously to the method for Example 9(c). Yield: 7.00 g (71%, hydrochloride); melting point 202° C.-206° C.

(d) 6-benzyloxy-8-{1-hydroxy-2-[2-(4-isopropylphenyl)-1,1-dimethylethylamino]ethyl}-4H-benzo[1,4]oxazin-3-one 2.18 g (6.1 mmol) of benzyloxy-8-(2-ethoxy-2-hydroxyacetyl)-4H-benzo[1,4]oxazin-3-one and 1.1 g (5.8 mmol) of 2-(4-isopropylphenyl)-1,1-dimethylethylamine are stirred in 40 mL ethanol at 50° C.-80° C. for one hour. After cooling to ambient temperature, 0.24 g (6.3 mmol) sodium borohydride is added. The mixture is stirred for one hour, diluted with 5 mL acetone, and stirred for a further 30 minutes. The reaction mixture is acidified with hydrochloric acid, combined with 100 mL water and 80 mL ethyl acetate, and made alkaline with ammonia. The organic phase is separated off, dried with sodium sulfate, and freed from solvent. The residue is dissolved in 20 mL ethyl acetate and 10 mL water, acidified with concentrated hydrochloric acid and diluted with diethyl ether. After the addition of a crystallization aid, the solid precipitate is suction filtered and washed. White solid. Yield: 1.7 g (52%, hydrochloride); melting point: 220° C.-222° C.

(e) 6-hydroxy-8-{1-hydroxy-2-[2-(4-isopropylphenyl)-1,1dimethylethylamino]-ethyl}-4H-benzo[1,4]oxazin-3-one 1.6 g (3.0 mmol) of 6-benzyloxy-8-{1-hydroxy-2-[2-(4-isopropylphenyl)-1,1-dimethylethylamino]ethyl}-4H-benzo[1,4]oxazin-3-one is dissolved in methanol and hydrogenated with palladium on charcoal as catalyst at normal pressure and ambient temperature. The catalyst is suction filtered, the solvent distilled off, and the residue recrystallized from isopropanol. White solid. Yield: 1.1 g (85%, hydrochloride); melting point 248° C.-250° C.; mass spectrometry: [M+H]$^+$=399.

The (R)- and (S)-enantiomers of this example can be obtained by separating the racemate analogously to current methods of racemate cleaving known in the prior art.

EXAMPLE 9

8-{2-[2-(4-ethylphenyl)-1,1-dimethylethylamino]-1-hydroxyethyl}-6-hydroxy-4H-benzo[1,4]oxazin-3-one

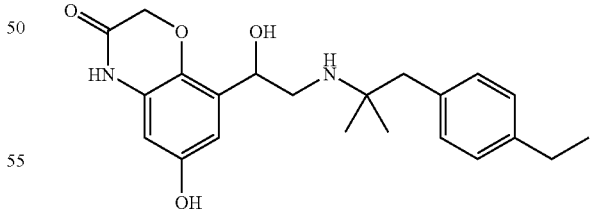

(a) 1-(4-ethylphenyl)-2-methylpropan-2-ol 14.8 g (90 mmol) of 1-(4-ethylphenyl)propan-2-one dissolved in diethyl ether is added dropwise to 39 mL of a 3 molar solution of methylmagnesium bromide in diethyl ether while being cooled with an ice bath in such a way that the temperature does not exceed 30° C. After the addition has ended, the reaction mixture is refluxed for 1.5 hours and then hydrolyzed with 10% ammonium chloride solution. After the removal of the organic phase, the aqueous phase is extracted with diethyl ether. The combined ether phases are washed with water, dried with sodium sulfate, and evaporated down. The oil thus obtained is further reacted directly. Yield: 15.5 g (90%).

(b) N-[2-(4-ethylphenyl)-1,1-dimethylethyl]acetamide 6.2 mL of concentrated sulfuric acid is added dropwise to 15.5 g (87 mmol) of 1-(4-ethylphenyl)-2-methylpropan-2-ol in 4.8 mL (91 mmol) acetonitrile and 15 mL glacial acetic acid within 15 minutes, during which time the temperature rises to 65° C. It is then stirred for one hour, diluted with ice water, and made alkaline with concentrated sodium hydroxide solution. After another 30 minutes' stirring, the solid precipitated is suction filtered and washed with water. The crude product is dissolved in ethyl acetate, dried with sodium sulfate, and evaporated down. The oil remaining is combined with petroleum ether, whereupon a solid is precipitated which is filtered off and dried. Yield: 16.3 g (85%); melting point 90° C.-92° C.

(c) 2-(4-ethylphenyl)-1,1-dimethylethylamine 16.3 g (74 mmol) of N-[2-(4-ethylphenyl)-1,1-dimethylethyl]acetamide and 8.0 g of potassium hydroxide are refluxed for 15 hours in 60 mL ethylene glycol. The reaction mixture is combined with ice water and extracted three times with diethyl ether. The combined organic phases are washed with water, dried with sodium sulfate, and freed from solvent. To prepare the hydrochloride, the crude product is dissolved in acetonitrile and ethereal hydrochloric acid and diethyl ether are added successively. The solid precipitated is suction filtered and dried. Yield: 11.0 g (69%, hydrochloride); melting point 165° C.-167° C.

(d) 6-benzyloxy-8-{2-[2-(4-ethylphenyl)-1,1-dimethylethylamino]-1-hydroxyethyl}-4H-benzo[1,4]oxazin-3-one The target compound is prepared analogously to the method for Example 8(d) from 2.14 g (6.0 mmol) of 6-benzyloxy-8-(2-ethoxy-2-hydroxyacetyl)-4H-benzo[1,4]oxazin-3-one and 1.0 g (5.6 mmol) of 2-(4-ethylphenyl)-1,1-dimethylethylamine. White solid. Yield: 1.7 g (54%, hydrochloride); melting point 210° C.-214° C.

(e) 8-{2-[2-(4-ethylphenyl)-1,1-dimethylethylamino]-1-hydroxyethyl}-6-hydroxy-4H-benzo[1,4]oxazin-3-one The hydrogenolysis of 1.45 g (2.75 mmol) of 6-benzyloxy-8-{2-[2-(4-ethylphenyl)-1,1-dimethylethylamino]-1-hydroxyethyl}-4H-benzo[1,4]oxazin-3-one according to the method for Example 8(e) yields the target compound in the form of a white solid. Yield: 1.07 g (92%; hydrochloride); melting point 266° C.-269° C.; mass spectrometry: [M+H]$^+$=385.

The (R)- and (S)-enantiomers of this example can be obtained by separating the racemate analogously to current methods of racemate cleaving known in the prior art.

EXAMPLE 10

8-{2-[2-(4-Fluoro-3-methylphenyl)-1,1-dimethylethylamino]-1-hydroxyethyl}-6-hydroxy-4H-benzo[1,4]oxazin-3-one

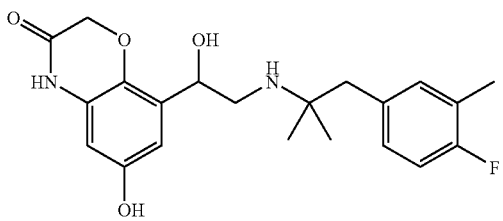

(a) 1-fluoro-2-methyl-4-(2-methylpropenyl)benzene 100 mL of a 0.5 molar solution of 4-fluoro-3-methylphenylmagnesium bromide in THF are combined with 4.7 mL (50 mmol) isopropylaldehyde within 30 minutes, while the temperature rises to 45° C. The mixture is stirred for 30 minutes, refluxed for 1 hour, and then hydrolyzed with 10% ammonium chloride solution. After separation of the organic phase, extraction is carried out with diethyl ether. The organic phases are combined, dried, and evaporated down. The alcohol thus obtained is dissolved in 100 mL toluene, combined with 1 g of p-toluenesulfonic acid monohydrate, and refluxed for three hours using the water separator. The reaction mixture is poured onto water and made alkaline with concentrated sodium hydroxide solution. After separation of the organic phase, it is washed with water, dried with sodium sulfate, and freed from solvent. Fractional distillation of the residue yields the product in the form of a colorless liquid (boiling point 80° C.-85° C./10 mbar). Yield: 4.1 g (50%).

(b) N-[2-(4-fluoro-3-methylphenyl)-1,1-dimethylethyl]formamide 4.9 mL concentrated sulfuric acid are added dropwise at 5° C.-15° C. to 1.5 g (31 mmol) sodium cyanide in 5 mL glacial acetic acid. Then the mixture is combined with 3.9 g (24 mmol) of 1-fluoro-2-methyl-4-(2-methylpropenyl)benzene, dissolved in 10 mL glacial acetic acid, and stirred for 1 hour at 50° C.-60° C. The reaction mixture is diluted with ice water, made alkaline with concentrated sodium hydroxide solution, and extracted with dichloromethane. The organic phase is dried with sodium sulfate and freed from solvents in vacuo. The slightly yellow oil thus obtained is further reacted directly. Yield: 4.3 g (87%).

(c) 2-(4-fluoro-3-methylphenyl)-1,1-dimethylethylamine 4.3 g (20.6 mmol) of N-[2-(4-fluoro-3-methylphenyl)-1,1-dimethylethyl]formamide, 20 mL concentrated hydrochloric acid, and 20 mL water are refluxed for 2 hours. The reaction mixture is diluted with water, made alkaline with concentrated sodium hydroxide solution, and extracted with dichloromethane. The organic phases are dried with sodium sulfate and evaporated down. The residue is dissolved in ethyl acetate, combined with ethereal hydrochloric acid, and cooled. The crystals precipitated are suction filtered and washed with diethyl ether and dried. White solid. Yield: 3.9 g (87%, hydrochloride); melting point 196° C.-198° C.

(d) 6-benzyloxy-8-{2-[2-(4-fluoro-3-methylphenyl)-1,1-dimethylethylamino]-1-hydroxyethyl}-4H-benzo[1,4]oxazin-3-one 1.10 g (3.1 mmol) of benzyloxy-8-(2-ethoxy-2-hydroxyacetyl)-4H-benzo[1,4]oxazin-3-one and 0.50 g (2.8 mmol) of 2-(4-fluoro-3-methylphenyl)-1,1-dimethylethylamine are reacted and worked up analogously to the method for Example 8(d). White solid. Yield: 0.75 g (47%, hydrochloride); melting point 228° C.-230° C.

(e) 8-{2-[2-(4-fluoro-3-methylphenyl)-1,1-dimethylethylamino]-1-hydroxyethyl}-6-hydroxy-4H-benzo[1,4]oxazin-3-one The hydrogenation of 0.70 g (1.4 mmol) of 6-benzyloxy-8-{2-[2-(4-fluoro-3-methylphenyl)-1,1-dimethylethylamino]-1-hydroxyethyl}-4H-benzo[1,4]oxazin-3-one yields the target compound as a white solid. Yield: 0.50 g (87%, hydrochloride); melting point 278° C.-280° C.; mass spectroscopy: [M+H]$^+$=389.

The (R)- and (S)-enantiomers of this example can be obtained by separating the racemate analogously to current methods of racemate cleaving known in the prior art.

EXAMPLE 11

8-{2-[2-(4-fluoro-2-methylphenyl)-1,1-dimethyl-ethylamino]-1-hydroxyethyl}-6-hydroxy-4H-benzo[1,4]oxazin-3-one

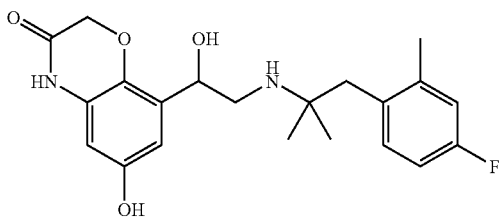

(a) 1-(4-fluoro-2-methylphenyl)-2-methylpropyl acetate 500 mL of a 0.5 molar solution of 4-fluoro-6-methylphenylmagnesium bromide and 23.2 mL (260 mmol) isopropylaldehyde are reacted analogously to Example 10(a). After hydrolysis with 10% ammonium chloride solution, the aqueous phase is separated off and extracted with diethyl ether. The combined organic phases are dried with sodium sulfate and evaporated down. The alcohol thus obtained is then dissolved in 50 mL acetic anhydride, combined with 1 mL concentrated sulfuric acid, and refluxed for three hours. Then the reaction mixture is poured onto water, stirred for a further hour, and made alkaline. It is extracted with dichloromethane, the organic phases are dried with sodium sulfate, and the solvents are distilled off. Fractional distillation of the residue yields the product in the form of a colorless liquid (boiling point: 105° C.-110° C./8 mbar). Yield 29.0 g (52%).

(b) N-[2-(4-fluoro-2-methylphenyl)-1,1-dimethylethyl]formamide 29.0 g (130 mmol) of 1-(4-fluoro-2-methylphenyl)-2-methylpropyl acetate is reacted and worked up analogously to the method for Example 10(b). Yellow oil. Yield: 27.0 g (99%).

(c) 2-(4-fluoro-2-methylphenyl)-1,1-dimethylethylamine

In order to prepare the amine, 27.0 g (130 mmol) of N-[2-(4-fluoro-2-methylphenyl)-1,1-dimethylethyl]formamide is reacted as described in the method for Example 10(c). White solid. Yield: 15.5 g (55%, hydrochloride); melting point: 277° C.-280° C.

(d) 6-benzyloxy-8-{2-[2-[4-fluoro-2-methylphenyl)-1,1-dimethylethylamino]-1-hydroxyethyl}-4H-benzo[1,4]oxazin-3-one Prepared analogously to the method for Example 8(d) from 0.95 g (2.66 mmol) of benzyloxy-8-(2-ethoxy-2-hydroxyacetyl)-4H-benzo[1,4]oxazin-3-one and 0.43 g (2.37 mmol) of 2-(4-fluoro-2-methylphenyl)-1,1-dimethylethylamine. Yield: 0.75 g (55%, hydrochloride); melting point 233° C.-236° C.

(e) 8-{2-[2-(4-fluoro-2-methylphenyl)-1,1-dimethylethylamino]-1-hydroxyethyl}-6-hydroxy-4H-benzo[1,4]oxazin-3-one The debenzylation of 0.70 g (1.36 mmol) of 6-benzyloxy-8-{2-[2-[4-fluoro-2-methylphenyl)-1,1-dimethylethylamino]-1-hydroxyethyl}-4H-benzo[1,4]oxazin-3-one yields the target compound in the form of a white solid. Yield: 0.50 g (87%, hydrochloride); melting point 278° C.-280° C.; mass spectroscopy: [M+H]$^+$=389.

The (R)- and (S)-enantiomers of this example can be obtained by separating the racemate analogously to current methods of racemate cleaving known in the prior art.

EXAMPLE 12

8-{2-[2-(2,4-difluorophenyl)-1,1-dimethylethylamino]-1-hydroxyethyl}-6-hydroxy-4H-benzo[1,4]oxazin-3-one

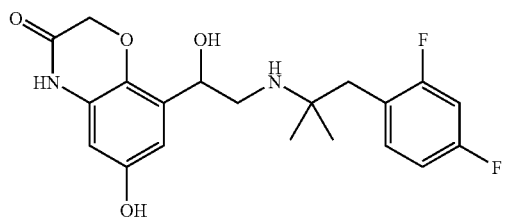

(a) 1-(2,4-difluorophenyl)-2-methylpropan-2-ol 11.0 mL acetone, diluted with 50 mL diethyl ether, is added dropwise to a solution of 500 mL of 0.25 molar 2,4-difluorobenzylmagnesium bromide in diethyl ether within 20 minutes. Then the mixture is refluxed for 1.5 hours and then hydrolyzed with 10% ammonium chloride solution. The ether phase is separated off, washed with water, dried with sodium sulfate, and evaporated down. The fractional distillation of the residue yields the alcohol as a colorless liquid (boiling point: 70° C.-73° C./2 mmbar). Yield: 20.0 g (86%).

(b) N-[2-(2,4-difluorophenyl]-1,1-dimethylethyl]formamide

Ritter reaction with 20 g (110 mmol) of 1-(2,4-difluorophenyl)-2-methylpropan-2-ol according to the method described for Example 10(b). Yellow oil. Yield: 22.0 g (94%).

(c) 2-(2,4-difluorophenyl)-1,1-dimethylethylamine

Reaction of 22.0 g (100 mmol) of N-[2-(2,4-difluorophenyl]-1,1-dimethylethyl]formamide analogously to the method for Example 10(c). Yield: 16.0 g (72%, hydrochloride); melting point: 201° C.-203° C.

(d) 6-benzyloxy-8-{2-[2-(2,4-difluorophenyl)-1,1-dimethylethylamino]-1-hydroxyethyl}-4H-benzo[1,4]oxazin-3-one Reaction of 0.89 g (2.49 mmol) of benzyloxy-8-(2-ethoxy-2-hydroxyacetyl)-4H-benzo[1,4]oxazin-3-one and 0.40 g (2.16 mmol) of 2-(2,4-difluorophenyl)-1,1-dimethylethylamine in the manner described for Example 8(d). Yield: 0.80 g (62%, hydrochloride); melting point 245° C.-247° C.

(e) 8-{2-[2-(2,4-difluorophenyl)-1,1-dimethylethylamino]-1-hydroxyethyl}-6-hydroxy-4H-benzo[1,4]oxazin-3-one The hydrogenolysis of 0.70 g (1.35 mmol) of 6-benzyloxy-8-{2-[2-(2,4-difluorophenyl)-1,1-dimethylethylamino]-1-hydroxyethyl}-4H-benzo[1,4]oxazin-3-one yields the target compound as a white solid. Yield: 0.48 g (83%, hydrochloride); melting point 279° C.-280° C.; mass spectroscopy: [M+H]$^+$=393.

The (R)- and (S)-enantiomers of this example can be obtained by separating the racemate analogously to current methods of racemate cleaving known in the prior art.

EXAMPLE 13

8-{2-[2-(3,5-difluorophenyl)-1,1-dimethylethylamino]-1-hydroxyethyl}-6-hydroxy-4H-benzo[1,4]oxazin-3-one

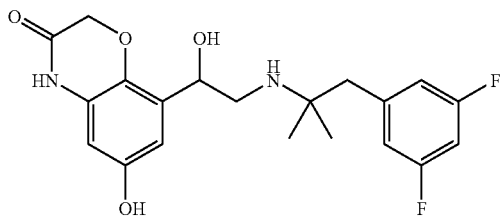

(a) 1-(3,5-difluorophenyl)-2-methylpropan-2-ol

The target compound is obtained by reacting a Grignard compound, prepared from 25.0 g (121 mmol) of 3,5-difluorobenzyl bromide, with 12.6 mL (171 mmol) of acetone. Yellow oil. Yield: 13.5 g (60%).

(b) 2-(3,5-difluorophenyl)-1,1-dimethylethylamine

The Ritter reaction of 5.5 g (29.5 mmol) of 1-(3,5-difluorophenyl)-2-methylpropan-2-ol and 1.8 g of sodium cyanide yields 7.0 g of formamide, which is treated with hydrochloric acid to cleave the formyl group. Slightly yellow oil. Yield: 4.6 g (75%).

(c) 6-benzyloxy-8-{2-[2-(3,5-difluorophenyl)-1,1-dimethylethylamino]-1-hydroxyethyl}-4H-benzo[1,4]oxazin-3-one Prepared from 1.73 g (4.84 mmol) of benzyloxy-8-(2-ethoxy-2-hydroxyacetyl)-4H-benzo[1,4]oxazin-3-one and 0.80 g (4.32 mmol) of 2-(3,5-difluorophenyl)-1,1-dimethylethylamine in the usual way. Yield: 1.50 g (58%, hydrochloride); melting point: 240° C.-244° C.

(d) 8-{2-[2-(3,5-difluorophenyl)-1,1-dimethylethylamino]-1-hydroxyethyl}-6-hydroxy-4H-benzo[1,4]oxazin-3-one Hydrogenolysis of 1.30 g (2.43 mmol) of 6-benzyloxy-8-{2-[2-(3,5-difluorophenyl)-1,1-dimethylethylamino]-1-hydroxyethyl}-4H-benzo[1,4]oxazin-3-one yields the target compound as a white solid. Yield: 0.90 g (86%, hydrochloride); melting point 150° C.-158° C.; mass spectroscopy: [M+H]$^+$=393.

The (R)- and (S)-enantiomers of this example can be obtained by separating the racemate analogously to current methods of racemate cleaving known in the prior art.

EXAMPLE 14

8-{2-[2-(4-ethoxyphenyl)-1,1-dimethylethylamino]-1-hydroxyethyl}-6-hydroxy-4H-benzo[1,4]oxazin-3-one

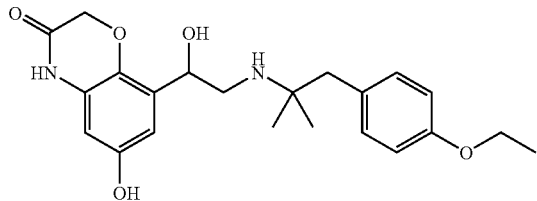

(a) benzyl [2-(4-ethoxyphenyl)-1,1-dimethylethyl]carbaminate 15.0 g (50 mmol) of benzyl [2-(4-hydroxyphenyl)-1,1-dimethylethyl]carbaminate is stirred with 7.5 mL (92 mmol) ethyl iodide and 21 g (150 mmol) potassium carbonate for 10 hours at 90° C.-100° C. The reaction mixture is combined with ethyl acetate, washed twice with water, and dried with sodium sulfate. After the solvents have been distilled off, a yellow oil remains (15.0 g, 92%), which is further reacted directly.

(b) 2-(4-ethoxyphenyl)-1,1-dimethylethylamine

A solution of 15.0 g (49 mmol) benzyl [2-(4-ethoxyphenyl)-1,1-dimethylethyl]-carbaminate in 100 mL glacial acetic acid is combined with 2 g palladium on charcoal (10%) and then hydrogenated at 5 bar and 40° C. to 50° C. The catalyst is filtered off and the filtrate is freed from solvent. The residue is dissolved in a little water, made alkaline with concentrated sodium hydroxide solution, and extracted with ethyl acetate. The organic phase is washed with water, dried with sodium sulfate, and evaporated down. The crude product is dissolved in acetonitrile and acidified with ethereal hydrochloric acid. The solid precipitated after the addition of diethyl ether is suction filtered and dried. Yield: 8.8 g (hydrochloride, 84%); melting point 198° C.-200° C.

(c) 6-benzyloxy-8-{2-[2-(4-ethoxyphenyl)-1,1-dimethylethylamino]-1-hydroxyethyl}-4H-benzo[1,4]oxazin-3-one 2.14 g (6.0 mmol) of 6-benzyloxy-8-(2-ethoxy-2-hydroxyacetyl)-4H-benzo[1,4]oxazin-3-one and 1.0 g (5.2 mmol) of 2-(4-ethoxyphenyl)-1,1-dimethylethylamine are stirred in 40 mL ethanol for one hour at 50° C.-80° C. After cooling to ambient temperature, 0.23 g (6.0 mmol) of sodium borohydride are added and the mixture is stirred for a further hour. The reaction mixture is combined with 5 mL acetone, stirred for 30 minutes, acidified with glacial acetic acid, and evaporated down. The residue is combined with water and ethyl acetate and made alkaline. The organic phase is separated off, washed with water, dried with sodium sulfate, and freed from solvent in vacuo. The residue is dissolved again in ethyl acetate and water, combined with concentrated hydrochloric acid, and diluted with diethyl ether. The solid precipitated is suction filtered and washed with diethyl ether. White solid. Yield: 2.0 g (61%, hydrochloride); melting point: 214° C.-216° C.

(d) 8-{2-[2-(4-ethoxyphenyl)-1,1-dimethylethylamino]-1-hydroxyethyl}-6-hydroxy-4H-benzo[1,4]oxazin-3-one 1.5 g (2.8 mmol) of 6-benzyloxy-8-{2-[2-(4-ethoxyphenyl)-1,1-dimethylethylamino]-1-hydroxyethyl}-4H-benzo[1,4]oxazin-3-one in 80 mL methanol are hydrogenated with 250 mg palladium on charcoal (10%) as catalyst at ambient temperature and normal pressure. The catalyst is suction filtered and the filtrate is evaporated down. The residue is dissolved in 5 mL ethanol by heating, seeded, and diluted with ethyl acetate. The solid precipitated is filtered off and washed. White solid. Yield 1.0 g (83%, hydrochloride); melting point: 232° C.-235° C.; mass spectrometry: [M+H]$^+$=401.

The (R)- and (S)-enantiomers of this example can be obtained by separating the racemate analogously to current methods of racemate cleaving known in the prior art.

EXAMPLE 15

8-{2-[2-(3,5-dimethylphenyl)-1,1-dimethylethylamino]-1-hydroxyethyl}-6-hydroxy-4H-benzo[1,4]oxazin-3-one

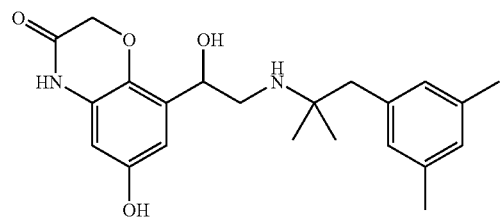

(a) 1-(3,5-dimethylphenyl)-2-methylpropanol-2-ol

Obtained by reacting ethyl (3,5-dimethylphenyl)acetate with methylmagnesium bromide.

(b) 2-(3,5-dimethylphenyl)-1,1-dimethylethylamine

By reacting 6.00 g (34 mmol) of 1-(3,5-dimethylphenyl)-2-methylpropanol-2-ol and 2.00 g (41 mmol) of sodium cyanide in a Ritter reaction, 2.40 g of 2-(3,5-dimethylphenyl)-1,1-dimethylethylformamide (35% yield) is obtained. To liberate the amine, the formamide (2.40 g, 11.7 mmol) is treated with hydrochloric acid. The method and working up are analogous to the method for Example 10(c). Oil. Yield: 1.70 g (82%); mass spectroscopy: $[M+H]^+=178$.

(c) 6-benzyloxy-8-{2-[2-(3,5-dimethylphenyl)-1,1-dimethylethylamino]-1-hydroxyethyl}-4H-benzo[1,4]oxazin-3-one Prepared analogously to the method for Example 8(d) from 1.47 g (4.1 mmol) of benzyloxy-8-(2-ethoxy-2-hydroxyacetyl)-4H-benzo[1,4]oxazin-3-one and 0.65 g (3.7 mmol) of 2-(3,5-dimethylphenyl)-1,1-dimethylethylamine. Yield: 1.1 g (51%, hydrochloride); melting point: 220° C.-222° C.

(d) 8-{2-[2-(3,5-dimethylphenyl)-1,1-dimethylethylamino]-1-hydroxyethyl}-6-hydroxy-4H-benzo[1,4]oxazin-3-one The target compound was obtained after hydrogenolysis of 0.90 g (1.71 mmol) of 6-benzyloxy-8-{2-[2-(3,5-dimethylphenyl)-1,1-dimethylethylamino]-1-hydroxyethyl}-4H-benzo[1,4]oxazin-3-one and recrystallization of the crude product from isopropanol. White solid. Yield: 0.50 g (69%, hydrochloride); melting point: 235° C.-238° C.; mass spectroscopy: $[M+H]^+=385$.

The (R)- and (S)-enantiomers of this example can be obtained by separating the racemate analogously to current methods of racemate cleaving known in the prior art.

EXAMPLE 16

4-(4-{2-[2-hydroxy-2-(6-hydroxy-3-oxo-3,4-dihydro-2H-benzo[1,4]oxazin-8-yl)ethylamino]-2-methylpropyl}phenoxy)butyric acid

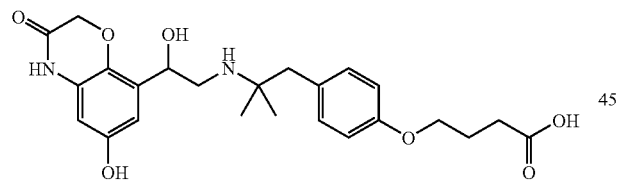

(a) ethyl 4-[4-(2-amino-2-methylpropyl)-phenoxy]-butyrate 4.5 g (15.0 mmol) of benzyl [2-(4-hydroxyphenyl)-1,1-dimethylethyl]carbaminate, 2.3 mL (16.0 mmol) of ethyl 4-bromobutyrate, 2.3 g (16.6 mmol) of potassium carbonate, and 0.3 g (1.8 mmol) of potassium iodide in 20 mL dimethylformamide are heated to 120° C. for 13 hours. The reaction mixture is diluted with ethyl acetate and washed successively with water, sodium hydroxide solution, and water. The organic phase is dried with sodium sulfate and evaporated down. The residue is purified by chromatography (eluent: cyclohexane-ethyl acetate (9:1)). 5.0 g of a yellow oil is isolated which is dissolved in 50 mL acetic acid and hydrogenated with 1.0 g palladium on charcoal as catalyst at 40° C. and 3 bar. The catalyst is filtered off and the filtrate is freed from solvent. The residue is dissolved in diethyl ether and combined with ethereal hydrochloric acid. The solid precipitated is suction filtered and dried. Yield: 2.9 g (66% in two stages, hydrochloride); melting point: 103° C.-105° C.

(b) ethyl 4-(4-{2-[2-(6-benzyloxy-3-oxo-3,4-dihydro-2H-benzo[1,4]oxazin-8-yl)-2-hydroxyethylamino]-2-methylpropyl}phenoxy)butyrate 1.20 g (3.36 mmol) of benzyloxy-8-(2-ethoxy-2-hydroxyacetyl)-4H-benzo[1,4]oxazin-3-one and 0.90 g (3.22 mmol) of ethyl 4-[4-(2-amino-2-methylpropyl)phenoxy]butyrate are reacted in the manner described for Example 8(d). The crude product is dissolved in 10 mL ethyl acetate and 10 mL water and combined with oxalic acid with stirring. The solution is diluted with diethyl ether and the solid precipitated is suction filtered and washed with diethyl ether. Yield: 1.20 g (54%, oxalate); melting point 223° C.-227° C.

(c) 4-(4-{2-[2-(6-benzyloxy-3-oxo-3,4-dihydro-2H-benzo[1,4]oxazin-8-yl)-2-hydroxyethylamino]-2-methylpropyl}phenoxy)butyric acid A solution of 1.00 g (1.73 mmol) of ethyl 4-(4-{2-[2-(6-benzyloxy-3-oxo-3,4-dihydro-2H-benzo-[1,4]oxazin-8-yl)-2-hydroxyethylamino]-2-methylpropyl}phenoxy)butyrate in 25 mL methanol is combined with 2.5 mL of 1 N sodium hydroxide solution, refluxed for 30 minutes, and then neutralized with 1 N hydrochloric acid. The solution is evaporated down and the residual oil is dissolved by heating in 5 mL of n-butanol. After the addition of a crystallization aid, a solid is precipitated out which is suction filtered and washed with acetone and diethyl ether. Yield: 0.75 g (79%); melting point: 216° C.-218° C.

(d) 4-(4-{2-[2-hydroxy-2-(6-hydroxy-3-oxo-3,4-dihydro-2H-benzo[1,4]oxaazin-8-yl)-ethylamino]-2-methylpropyl}phenoxy)butyric acid 0.70 g (1.28 mmol) of 4-(4-{2-[2-(6-benzyloxy-3-oxo-3,4-dihydro-2H-benzo[1,4]oxazin-8-yl)-2-hydroxyethylamino]-2-methylpropyl}phenoxy)butyric acid is dissolved in 25 mL methanol and 2 mL acetic acid and hydrogenated in the presence of 150 mg palladium on charcoal (10%) at ambient temperature and normal pressure. The catalyst is filtered off and the filtrate is freed from solvent. The product is obtained by crystallization from a methanol-acetone mixture. Yield: 0.40 g (68%); melting point: 201° C.-204° C.; mass spectroscopy: $[M+H]^+=459$.

The (R)- and (S)-enantiomers of this example can be obtained by separating the racemate analogously to current methods of racemate cleaving known in the prior art.

EXAMPLE 17

8-{2-[2-(3,4-difluorophenyl)-1,1-dimethylethylamino]-1-hydroxyethyl}-6-hydroxy-4H-benzo[1,4]oxazin-3-one

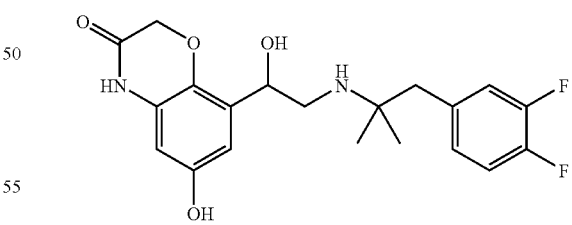

(a) 1-(3,4-difluorophenyl)-2-methylpropan-2-ol

From 23.0 g (111 mmol) of 3,4-difluorobenzyl bromide a Grignard is prepared, which is then reacted with 11.6 mL (158 mmol) of acetone. Slightly yellow oil. Yield: 9.7 g (47%); $R_f$ value: 0.55 (ethyl acetate-petroleum ether (1:3)).

(b) N-[2-(3,4-difluorophenyl)-1,1-dimethylethyl]formamide

The target compound is obtained by a Ritter reaction with 4.0 g (21.5 mmol) of 1-(3,4-difluorophenyl)-2-methylpropan-2-ol. Slightly yellow oil. Yield: 4.0 g (87%); mass spectrometry: $[M+H]^+=214$.

(c) 2-(3,4-difluorophenyl)-1,1-dimethylethylamine 4.00 g (18.5 mmol) of N-[2-(3,4-difluorophenyl)-1,1-dimethylethyl]formamide is dissolved in ethanol, combined with concentrated hydrochloric acid, and refluxed overnight. The reaction solution is poured onto ice water, made alkaline with sodium hydroxide, and extracted with tert-butylmethyl ether. The organic phases are washed with water, dried with sodium sulfate, and evaporated down. Yellow oil. Yield: 3.2 g (92%); mass spectrometry: $[M+H]^+=186$.

(d) 8-{2-[2-(3,4-difluorophenyl)-1,1-dimethylethylamino]-1-hydroxyethyl}-6-hydroxy-4H-benzo[1,4]oxazin-3-one 357 mg (1 mmol) of 6-benzyloxy-8-(2-ethoxy-2-hydroxyacetyl)-4H-benzo[1,4]oxazin-3-one and 185 mg (1 mmol) of 2-(3,4-difluorophenyl)-1,1-dimethylethylamine are stirred for 30 minutes in 5 mL tetrahydrofuran at ambient temperature. It is cooled to 0° C. and, under an argon atmosphere, 1.5 mL of a 2 molar solution of lithium borohydride in tetrahydrofuran is added dropwise. The mixture is stirred for 30 minutes at ambient temperature, combined with 10 mL dichloromethane, and 3 mL water, stirred for a further hour and then filtered through an EXTRELUT® column. The eluate containing the ethanol amine is freed from solvent. The residue is dissolved in methanol and hydrogenated with palladium on charcoal (10%) as catalyst at 2.5 bar and ambient temperature. Then the catalyst is separated off and the crude product is purified by chromatography. White solid. Yield: 31 mg (6%, trifluoroethyl acetate); mass spectroscopy: $[M+H]^+= 393$.

The (R)- and (S)-enantiomers of this example can be obtained by separating the racemate analogously to current methods of racemate cleaving known in the prior art.

EXAMPLE 18

8-{2-[2-(2-chloro-4-fluorophenyl)-1,1-dimethylethylamino]-1-hydroxyethyl}-6-hydroxy-4H-benzo[1,4]oxazin-3-one

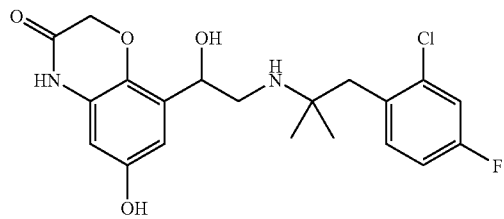

(a) 1-(2-chloro-4-fluorophenyl)-2-methylpropan-2-ol

Prepared from 20 g (97 mmol) of methyl (2-chloro-4-fluorophenyl)acetate and 98 mL of a 3 molar solution of methylmagnesium bromide analogously to the method for Example 8(a).

(b) N-[2-(2-chloro-4-fluorophenyl)-1,1-dimethylethyl]formamide 7.5 g (37 mmol) of 1-(2-chloro-4-fluorophenyl)-2-methylpropan-2-ol was reacted and worked up according to the method described for Example 10(b). The oil thus obtained was chromatographed for further purification on a short silica gel column (petroleum ether-ethyl acetate (9:1)). Oil. Yield 7.4 g (87%); mass spectrometry: $[M+H]^+=230/232$.

(c) 2-(2-chloro-4-fluorophenyl)-1,1-dimethylethylamine

Reaction of 7.4 g (32 mmol) of N-[2-(2-chloro-4-fluorophenyl)-1,1-dimethylethyl]-formamide as described in the method for Example 17(c). Brown oil. Yield: 5.14 g (79%); mass spectrometry: $[M+H]^+=202/204$.

(d) 8-{2-[2-(2-chloro-4-fluorophenyl)-1,1-dimethylethylamino]-1-hydroxyethyl}-6-hydroxy-4H-benzo[1,4]oxazin-3-one 357 mg (1 mmol) of 6-benzyloxy-8-(2-ethoxy-2-hydroxyacetyl)-4H-benzo[1,4]oxazin-3-one and 202 mg (1 mmol) of 2-(2-chloro-4-fluorophenyl)-1,1-dimethylethylamine are reacted with lithium borohydride analogously to the method for Example 10(d). To debenzylate the ethanolamine thus obtained, it is dissolved in 3 mL of dichloromethane and cooled to −78° C. At this temperature, 2 mL of a 1 molar solution of boron tribromide in dichloromethane is added and the mixture is slowly allowed to come up to ambient temperature. The reaction mixture is combined with 10 mL dichloromethane and 3 mL water and filtered through an EXTRELUT® column. The eluate is freed from solvent and the residue is purified by chromatography. White solid. Yield: 70 mg (13%, trifluoroethyl acetate); mass spectroscopy: $[M+H]^+= 409/11$.

The (R)- and (S)-enantiomers of this example can be obtained by separating the racemate analogously to current methods of racemate cleaving known in the prior art.

EXAMPLE 19

8-{2-[2-(4-chlorophenyl)-1,1-dimethylethylamino]-1-hydroxyethyl}-6-hydroxy-4H-benzo[1,4]oxazin-3-one

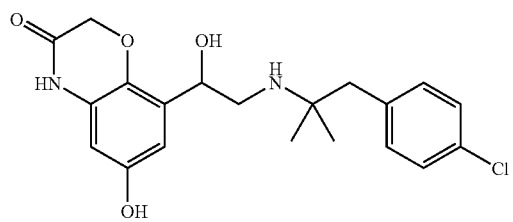

A solution of 300 mg (0.91 mmol) of 6-benzyloxy-8-(2,2-dihydroxy-acetyl)-4H-benzo[1,4]oxazin-3-one and 200 mg (1.09 mmol) of 2-(4-chlorophenyl)-1,1-dimethylethylamine in 3 mL ethanol was combined with molecular sieve and stirred for 90 minutes at 80° C. It was allowed to cool to ambient temperature, 35 mg (0.91 mmol) of sodium borohydride was added, and the mixture was stirred for 1 hour. Then the reaction mixture was combined with sodium hydrogen carbonate solution and extracted with ethyl acetate. The combined organic phases were freed from solvent and the residue was chromatographed (eluent: hexane-ethyl acetate-methanol), yielding 305 mg of ethanolamine. This was dissolved in 3 mL dichloromethane and cooled to −78° C. under an argon atmosphere. 3 mL of a 1 molar solution of boron tribromide in dichloromethane were added dropwise and the mixture was stirred for one hour at −78° C. and for 20 minutes at ambient temperature. Then at −78° C., 3 mL of concentrated ammonia solution was added dropwise and the mixture was stirred for 5 minutes. The reaction mixture was combined with ammonium chloride solution and extracted with ethyl acetate. The combined organic phases were evaporated down and the residue was further purified by chromatography (silica gel; eluent: dichloromethane-methanol+1% ammonia). Beige-colored solid: 93 mg (26%); mass spectrometry: $[M+H]^+=391$.

EXAMPLE 20

8-{2-[2-(4-bromophenyl)-1,1-dimethylethylamino]-1-hydroxyethyl}-6-hydroxy-4H-benzo[1,4]oxazin-3-one

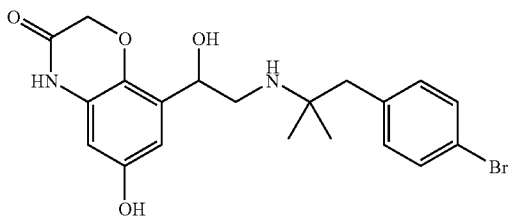

The preparation of the ethanolamine and debenzylation were carried out as described in Example 19 from 300 mg (0.91 mmol) of 6-benzyloxy-8-(2,2-dihydroxy-acetyl)-4H-benzo[1,4]oxazin-3-one and 250 mg (1.09 mmol) of 2-(4-bromophenyl)-1,1-dimethylethylamine. Beige solid. Yield: 54 mg (14%); mass spectrometry: $[M+H]^+=435, 437$.

The (R)- and (S)-enantiomers of this example can be obtained by separating the racemate analogously to current methods of racemate cleaving known in the prior art.

EXAMPLE 21

8-{2-[2-(4-fluorophenyl)-1,1-dimethylethylamino]-1-hydroxyethyl}-6-hydroxy-4H-benzo[1,4]oxazin-3-one

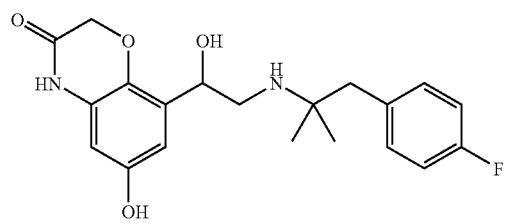

300 mg (0.91 mmol) of 6-benzyloxy-8-(2,2-dihydroxy-acetyl)-4H-benzo[1,4]oxazin-3-one and 183 mg (1.09 mmol) of 2-(4-fluorophenyl)-1,1-dimethylethylamine were dissolved in 3 mL of ethanol. Molecular sieve was added and the mixture was heated to 80° C. for 30 minutes. After cooling to ambient temperature, 35 mg (0.91 mmol) of sodium borohydride was added. The mixture was stirred for 1 hour at ambient temperature, then sodium hydrogen carbonate solution was added to the reaction mixture and it was extracted with ethyl acetate. The organic phases were evaporated down and the residue was chromatographed (eluent: hexane-ethyl acetate-methanol). The ethanolamine thus obtained (223 mg) was dissolved in methanol to cleave the benzyl protecting group and hydrogenated with 150 mg palladium hydroxide as catalyst at ambient temperature and normal pressure. The catalyst was separated off by filtering through CELITE® filter agent, the filtrate was freed from solvent and the residue was chromatographed (silica gel; eluent: dichloromethane-methanol). Beige solid. Yield: 76 mg (22%); mass spectrometry: $[M+H]^+=375$.

The (R)- and (S)-enantiomers of this example can be obtained by separating the racemate analogously to current methods of racemate cleaving known in the prior art.

The following compounds of Formula 1 according to the invention may be obtained analogously to the synthesis examples described above:

EXAMPLE 22

8-{2-[2-(4-fluoro-3-methoxyphenyl)-1,1-dimethylethylamino]-1-hydroxyethyl}-6-hydroxy-4H-benzo[1,4]oxazin-3-one

EXAMPLE 23

8-{2-[2-(4-fluoro-2,6-dimethylphenyl)-1,1-dimethylethylamino]-1-hydroxyethyl}-6-hydroxy-4H-benzo[1,4]oxazin-3-one

EXAMPLE 24

8-{2-[2-(4-chloro-2-methylphenyl)-1,1-dimethylethylamino]-1-hydroxyethyl}-6-hydroxy-4H-benzo[1,4]oxazin-3-one

EXAMPLE 25

8-{2-[2-(4-chloro-3-fluorophenyl)-1,1-dimethylethylamino]-1-hydroxyethyl}-6-hydroxy-4H-benzo[1,4]oxazin-3-one

EXAMPLE 26

8-{2-[2-(4-chloro-2-fluorophenyl)-1,1-dimethylethylamino]-1-hydroxyethyl}-6-hydroxy-4H-benzo[1,4]oxazin-3-one

EXAMPLE 27

8-{2-[2-(3-chloro-4-fluorophenyl)-1,1-dimethylethylamino]-1-hydroxyethyl}-6-hydroxy-4H-benzo[1,4]oxazin-3-one

EXAMPLE 28

8-{2-[2-(2,6-difluoro-4-methoxyphenyl)-1,1-dimethylethylamino]-1-hydroxyethyl}-6-hydroxy-4H-benzo[1,4]oxazin-3-one

EXAMPLE 29

8-{2-[2-(2,5-difluoro-4-methoxyphenyl)-1,1-dimethylethylamino]-1-hydroxyethyl}-6-hydroxy-4H-benzo[1,4]oxazin-3-one

EXAMPLE 30

8-{2-[2-(4-fluoro-3,5-dimethylphenyl)-1,1-dimethylethylamino]-1-hydroxyethyl}-6-hydroxy-4H-benzo[1,4]oxazin-3-one

EXAMPLE 31

8-{2-[2-(3,5-dichlorophenyl)-1,1-dimethylethylamino]-1-hydroxyethyl}-6-hydroxy-4H-benzo[1,4]oxazin-3-one

EXAMPLE 32

8-{2-[2-(4-chloro-3-methylphenyl)-1,1-dimethylethylamino]-1-hydroxyethyl}-6-hydroxy-4H-benzo[1,4]oxazin-3-one

EXAMPLE 33

8-{2-[2-(3,4,5-trifluorophenyl)-1,1-dimethylethylamino]-1-hydroxyethyl}-6-hydroxy-4H-benzo[1,4]oxazin-3-one

EXAMPLE 34

8-{2-[2-(3-methylphenyl)-1,1-dimethylethylamino]-1-hydroxyethyl}-6-hydroxy-4H-benzo[1,4]oxazin-3-one; and

EXAMPLE 35

8-{2-[2-(3,4-dichlorophenyl)-1,1-dimethylethylamino]-1-hydroxyethyl}-6-hydroxy-4H-benzo[1,4]oxazin-3-one The compounds of general formula 1 may be used on their own or combined with other active substances of formula 1 according to the invention. The compounds of general formula 1 may optionally also be combined with other pharmacologically active substances. These include, in particular, anticholinergics, optionally other betamimetics, antiallergic agents, PDE-IV inhibitors, PAF-antagonists, leukotriene-antagonists, and corticosteroids and combinations of these active substances.

Examples of preferred anticholinergics which may be mentioned include ipratropium, oxitropium, and tiotropium salts. Pharmaceutical combinations which contain the abovementioned salts, in addition to the compounds of formula 1 according to the invention, preferably contain those salts of ipratropium, oxitropium, or tiotropium wherein the anion is selected from among the chloride, bromide, iodide, sulfate, phosphate, methanesulfonate, nitrate, maleate, acetate, citrate, fumarate, tartrate, oxalate, succinate, benzoate, and p-toluenesulfonate, optionally in the form of one of the solvates or hydrates thereof.

Within the scope of the present invention, the corticosteroids which may optionally be used in conjunction with the compounds of formula 1 may be compounds selected from among flunisolide, beclomethasone, triamcinolone, budesonide, fluticasone, mometasone, ciclesonide, rofleponide, and dexamethasone. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates, or furoates. In some cases, the corticosteroids may also occur in the form of their hydrates.

Within the scope of the present invention, the term dopamine agonists, which may optionally be used in conjunction with the compounds of formula 1, denotes compounds selected from among bromocriptine, cabergoline, alpha-dihydroergocryptine, lisuride, pergolide, pramipexol, roxindole, ropinirole, talipexole, terguride, and viozan. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of antiallergic agents which may be used according to the invention as a combination with the compound of formula 1 include epinastine, cetirizine, azelastine, fexofenadine, levocabastine, loratadine, mizolastine, ketotifene, emedastine, dimetindene, clemastine, bamipine, hexachloropheniramine, pheniramine, doxylamine, chlorophenoxamine, dimenhydrinate, diphenhydramine, promethazine, ebastine, desloratadine, and meclizine. Any reference to the abovementioned antiallergic agents also includes, within the scope of the present invention, a reference to any pharmacologically acceptable acid addition salts thereof which may exist.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A, and AWD-12-281. Any reference to the abovementioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid. According to the invention, the salts selected from among the acetate, hydrochloride, hydrobromide, sulfate, phosphate, and methanesulfonate are preferred in this context.

Suitable preparations for administering the compounds of formula 1 include, for example, tablets, capsules, suppositories, solutions, powders, etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate, or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilizers such as alkali metal salts of ethylenediaminetetraacetic acid, optionally using emulsifiers and/or dispersants, while if water is used as diluent, for example, organic solvents may optionally be used as solubilizers or dissolving aids, and the solutions may be transferred into injection vials or ampoules or infusion bottles.

Capsules containing one or more active substances or combinations of active substances may, for example, be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, chalk), synthetic mineral powders (e.g., highly dispersed silicic acid and silicates), sugars (e.g., cane sugar, lactose and glucose), emulsifiers (e.g., lignin, spent sulfite liquors, methylcellulose, starch, and polyvinylpyrrolidone) and lubricants (e.g., magnesium stearate, talc, stearic acid, and sodium lauryl sulfate).

For oral use, the tablets may obviously contain, in addition to the carriers specified, additives such as sodium citrate, calcium carbonate, and dicalcium phosphate together with various additional substances such as starch, preferably potato starch, gelatin, and the like. Lubricants such as magnesium stearate, sodium lauryl sulfate, and talc may also be used to produce the tablets. In the case of aqueous suspensions, the active substances may be combined with various flavor enhancers or colorings in addition to the above-mentioned excipients.

For administering the compounds of formula 1 for the treatment of COPD, it is particularly preferred according to the invention to use preparations or pharmaceutical formulations which are suitable for inhalation. Inhalable preparations include inhalable powders, propellant-containing metered-dose aerosols, or propellant-free inhalable solutions. Within the scope of the present invention, the term propellant-free inhalable solutions also includes concentrates or sterile inhalable solutions ready for use. The formulations which may be used within the scope of the present invention are described in more detail in the next part of the specification.

The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, or maltose), oligo- and polysaccharides (e.g., dextrans), polyalcohols (e.g., sorbitol, mannitol, or xylitol), salts (e.g., sodium chloride or calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 µm and 150 µm, most preferably between 15 µm and 80 µm. It may sometimes seem appropriate to add finer excipient fractions with an average particle size of 1 µm to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 µm to 10 µm, more preferably from 1 µm to 5 µm, is added to the excipient mixture. Processes for producing the inhalable powders according to the invention by grinding and micronizing and finally mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane, or isobutane and halohydrocarbons such as fluorinated derivatives of methane, ethane, propane, butane, cyclopropane, or cyclobutane. The abovementioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilizers, surfactants, antioxidants, lubricants, and pH adjusters. All these ingredients are known in the art.

The propellant-driven inhalation aerosols according to the invention mentioned above may be administered using inhalers known in the art, such as metered dose inhalers (MDIs).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid etc. Preferred inorganic acids are hydrochloric and sulfuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g., as flavorings, antioxidants or complexing agents, such as citric acid or ascorbic acid, for example. According to the invention, it is particularly preferred to use hydrochloric acid to adjust the pH.

If desired, the addition of edetic acid (EDTA) or one of the known salts thereof, sodium edetate, as stabilizer or complexing agent may be omitted in these formulations. Other embodiments may contain this compound or these compounds. In a preferred embodiment the content based on sodium edetate is less than 100 mg/100 mL, preferably less than 50 mg/100 mL, more preferably less than 20 mg/100 mL. Generally, inhalable solutions in which the content of sodium edetate is from 0 to 10 mg/100 mL are preferred.

Co-solvents and/or other excipients may be added to the propellant-free inhalable solutions. Preferred co-solvents are those which contain hydroxyl groups or other polar groups, e.g., alcohols, particularly isopropyl alcohol, glycols, particularly propyleneglycol, polyethyleneglycol, polypropyleneglycol, glycol ether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants and/or preservatives which guarantee or prolong the shelf life of the finished pharmaceutical formulation, flavorings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art. The preservatives mentioned above are preferably present in concentrations of up to 50 mg/100 mL, more preferably between 5 and 20 mg/100 mL.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation, the compounds of formula 1 are characterized by a high potency even at doses in the μg range. The compounds of formula 1 may also be used effectively above the μg range. The dosage may then be in the gram range, for example.

In another aspect, the present invention relates to the above-mentioned pharmaceutical formulations as such which are characterized in that they contain a compound of formula 1, particularly the above-mentioned pharmaceutical formulations which can be administered by inhalation.

The following examples of formulations illustrate the present invention without restricting its scope:

EXAMPLES OF PHARMACEUTICAL FORMULATIONS

| A. Tablets | per tablet |
|---|---|
| active substance 1 | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose, and some of the maize starch are mixed together. The mixture is screened, then moistened with a solution of polyvinylpyrrolidone in water, kneaded, wet granulated, and dried. The granules, the remaining maize starch and the magnesium stearate are screened and mixed together. The mixture is pressed into tablets of suitable shape and size.

| B. Tablets | per tablet |
|---|---|
| active substance 1 | 80 mg |
| lactose | 55 mg |
| maize starch | 190 mg |
| microcrystalline cellulose | 35 mg |
| polyvinylpyrrolidone | 15 mg |
| sodium carboxymethyl starch | 23 mg |
| magnesium stearate | 2 mg |
| | 400 mg |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C. Ampoule Solution | |
|---|---|
| active substance 1 | 50 mg |
| sodium chloride | 50 mg |
| water for inj. | 5 mL |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg, and 50 mg of active substance.

| D. Metering Aerosol | |
|---|---|
| active substance 1 | 0.005 |
| sorbitan trioleate | 0.1 |
| monofluorotrichloromethane and TG134a:TG227 (2:1) | to 100 |

The suspension is transferred into a conventional aerosol container with metering valve. Preferably 50 μl suspension are released on each actuation. The active substance may also be released in higher doses if desired (e.g., 0.02 wt.-%).

| E. Solutions (in mg/100 mL) | |
|---|---|
| active substance 1 | 333.3 mg |
| benzalkonium chloride | 10.0 mg |
| EDTA | 50.0 mg |
| HCl (1 N) | to pH 3.4 |

This solution can be prepared in the usual way.

| F. Inhalable Powder | |
|---|---|
| active substance 1 | 12 μg |
| lactose monohydrate | to 25 mg |

The inhalable powder is prepared in the usual way by mixing the individual ingredients.

We claim:

1. A method for the treatment of Chronic Obstructive Pulmonary Disease (COPD) comprising administration of a therapeutically effective amount of R-6-Hydroxy-8-{1-hydroxy-2[2-(4-methoxy-phenyl)-1,1-dimethyl-ethylamino]-ethyl}-4H-benzo[1,4]oxazin-3-one, or an acid addition salt thereof with a pharmacologically acceptable acid; and a pharmaceutically acceptable excipient or carrier.

2. A method for the treatment of Chronic Obstructive Pulmonary Disease (COPD) comprising administration of a therapeutically effective amount of R-8-{2-[2-(2,4-difluorophenyl)-1,1-dimethyl-ethylamino]-1-hydroxy-ethyl}-6-hydroxy-4H-benzo[1,4]oxazin-3-one, or an acid addition salt thereof with a pharmacologically acceptable acid; and a pharmaceutically acceptable excipient or carrier.

3. A method for the treatment of Chronic Obstructive Pulmonary Disease (COPD) comprising administration of a therapeutically effective amount of R-8-{2-[2-(3,5-difluorophenyl)-1,1-dimethyl-ethylamino]-1-hydroxy-ethyl}-6-hydroxy-4H-benzo[1,4]oxazin-3-one, or an acid addition salt thereof with a pharmacologically acceptable acid; and a pharmaceutically acceptable excipient or carrier.

4. A method for the treatment of Chronic Obstructive Pulmonary Disease (COPD) comprising administration of a therapeutically effective amount of R-8-{2-[2-(4-Ethoxyphenyl)-1,1-dimethyl-ethylamino]-1-hydroxy-ethyl}-6-hydroxy-4H-benzo[1,4]oxazin-3-one, or an acid addition salt thereof with a pharmacologically acceptable acid; and a pharmaceutically acceptable excipient or carrier.

5. A method for the treatment of Chronic Obstructive Pulmonary Disease (COPD) comprising administration of a therapeutically effective amount of R-8-{2-[2-(4-fluorophenyl)-1,1-dimethyl-ethylamino]-1-hydroxy-ethyl}-6-hydroxy-4H-benzo[1,4]oxazin-3-one, or an acid addition salt thereof with a pharmacologically acceptable acid; and a pharmaceutically acceptable excipient or carrier.

* * * * *